United States Patent [19]
Habermeyer

[11] Patent Number: 5,857,987
[45] Date of Patent: Jan. 12, 1999

[54] DEVICE FOR THE ENSHEATHING FIXATION OF EXTREMITIES AND EXTREMITY REGIONS

[76] Inventor: Peter Habermeyer, Hillerstrasse 6, D-70184 Stuttgart, Germany

[21] Appl. No.: 824,060

[22] Filed: Mar. 24, 1997

Related U.S. Application Data

[63] Continuation of Ser. No. 553,312, Nov. 20, 1995, abandoned.

[30] Foreign Application Priority Data

| May 21, 1993 | [DE] | Germany | G 93 07 550.2 |
| May 21, 1993 | [DE] | Germany | G 93 07 549.9 |
| May 21, 1993 | [DE] | Germany | G 93 07 548.0 |
| Nov. 13, 1993 | [DE] | Germany | G 93 17 421.7 |
| Mar. 12, 1994 | [DE] | Germany | G 94 04 210.1 |

[51] Int. Cl.⁶ ........................................ A61F 5/00
[52] U.S. Cl. ............................. 602/23; 36/120
[58] Field of Search ................. 602/5, 12, 10, 602/23, 27–29; 36/110, 117, 120, 140

[56] References Cited

U.S. PATENT DOCUMENTS

| 3,955,565 | 5/1976 | Johnson, Jr. . |
| 4,029,090 | 6/1977 | Dawson, Jr. . |
| 4,665,904 | 5/1987 | Lerman ........................... 602/27 |
| 4,803,975 | 2/1989 | Meyers . |
| 4,834,078 | 5/1989 | Biedermann ....................... 602/27 |
| 5,044,360 | 9/1991 | Jarke ............................ 602/27 X |
| 5,197,942 | 3/1993 | Brady ............................. 602/5 |
| 5,197,943 | 3/1993 | Link .............................. 602/5 |

FOREIGN PATENT DOCUMENTS

| 0355930 | 2/1990 | European Pat. Off. . |
| 0538695 | 4/1993 | European Pat. Off. . |
| 3228753 | 2/1984 | Germany . |
| 3826704 | 2/1990 | Germany ........................ 602/5 |
| 8605087 | 9/1986 | WIPO . |
| 9204880 | 4/1992 | WIPO . |
| 9324081 | 12/1993 | WIPO . |

*Primary Examiner*—Linda C. Dvorak
*Attorney, Agent, or Firm*—Friedrich Kueffner

[57] ABSTRACT

The device for the ensheathing fixation of extremities, more particularly for the treatment of extremity fractures of the lower leg and thigh, is comprised of a shell-like member (10) of one shell portion or of two reciprocally tightenable L-shaped shell portions (20, 30) possessing an approximately semi-circular cross-section which surround the extremity to be ensheathed, in which, between the shell portions (20, 30) and the extremity, at least one sleeve-like padding is provided whose contents can be evacuated, in whose interior located between the two padding walls, a large number of filling material particles which are movable relative to each other, are provided, while the wall areas of the shell-like member (10) are, at least in part, constructed so as to be latticed and/or ribbed (FIG. 2).

49 Claims, 32 Drawing Sheets

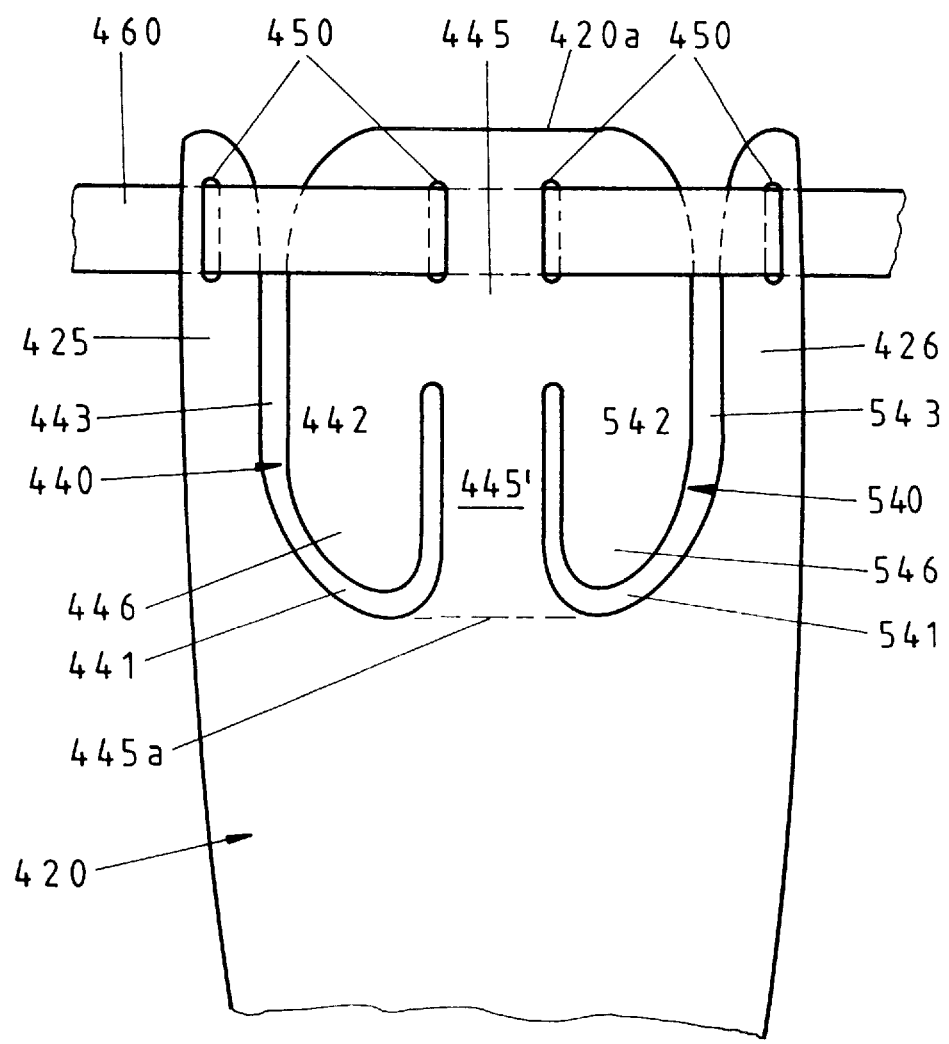

DEVICE FOR THE ENSHEATHING FIXATION OF EXTREMITIES AND EXTREMITY REGIONS

RELATED APPLICATION

This application is a continuation of application Ser. No. 08/553,312 filed Nov. 20, 1995, now abandoned.

FIELD OF THE INVENTION

The present invention relates to a device for the ensheathing fixation of extremities and extremity regions. More particularly, the invention relates to the treatment of extremity fractures within the area of the lower leg and thigh, and comprises a shell-like member possessing one shell portion or two L-shaped shell portions which can be tightened against each other. An approximately semicircular cross-section is provided which surrounds the extremity to be ensheathed. Between the shell portions and the extremity, at least one sleeve-like padding is provided whose contents can be emptied. In the interior regions, between the two padding walls, a plurality of filling material particles are provided which are moveable in relation to each other.

BACKGROUND

For the treatment of extremity fractures, casts or bandages made from plaster of Paris or their modern plastic variants are normally applied. Not only does the application of such casts or bandages call for considerable skill and relevant effort on the part of the staff, but frequently also leads to exceedingly vexatious pressure sores that develop due to edges or projections on the inside of the cast or bandage. After the reduction of the respective fracture, the patient is subjected to the painful phase of the bandages being applied afresh and having to wait for the plaster to set. Finally, as a rule, it is necessary to know when the casts or bandages are employed, to effect a replacement of this cast or bandage when, in the course of the fracture treatment, a detumescence of the limb in question takes place. This, too, is a costly and effort-intensive procedure and a painful experience for the patient.

A device is presently known from the WO 92/04880 for the ensheathing fixation of extremities and extremity regions. This device is provided especially for the treatment of extremity fractures within the area of the lower leg, thigh, forearm and upper arm, and possesses at least two mutually tightenable shell portions that surround the extremity to be ensheathed. Between the shell portions and the extremity, two moldable, vacuum-tight-constructed paddings fitted with at least one valve are provided, in which a large quantity of in particular small-grain filling material particles which are moveable relative to each other is to be found. The contents of the paddings can be emptied.

These known plaster of Paris and plastic casts and bandages presuppose a predetermined angular position between the foot and lower leg, in which case preference is given to the normal angular position of the joints at an angle of 90°. Once the cast or bandage has been applied, a change in the angular position is no longer possible. If, on the other hand, an operating cast or bandage is applied on the seam of the Achilles tendon, the procedure is that, subsequent to the operation, the lower leg is stood up vertically and raised to the maximal pes equinus position. Also in the case of a closed pes equinus plaster cast, the foot does not assume a normal angular position relative to the lower leg, but the positioning of the foot in relation to the lower leg is effected at an angle greater than 90°; often at an angle of 120° so that this angular position of the foot relative to the lower leg is preset and fixated. In this case, too, a change in the angular position is not possible.

In order to take remedial action here, it has already been proposed to utilize an angle adjusting or setting means between the foot portion and the leg portion of each shell portion, with the aid of which said components can be locked in a predetermined, but freely selectable, angular position.

The disadvantage associated with the plaster of Paris casts or bandages as well as of the devices stated in the foregoing resides in that they, in conformity with the required stability, still possess relatively great weight and practically prevent any air from being supplied to the ensheathed extremity regions. A further disadvantage of the aforedescribed device consists in that the internal dimensions of the shell portion are laid down constructionally and it is only possible to provide a balance with respect to different extremity diameters with the aid of paddings or other filling materials.

OBJECT AND SUMMARY OF THE INVENTION

The present invention takes remedial action here by providing a device with the same function as existing ones, but which, despite a high degree of inherent rigidity, is of low weight and makes a good air supply possible and which, in addition, renders possible an individual adaptation to differing extremity diameters and, particularly to the calf of the patient and which is universally applicable for various angular positions of the foot in relation to the lower leg.

This technical problem is resolved by means of the device described herein. According thereto and in accordance with the invention, the wall areas of the shell-like member are, at least in part, constructed so as to be latticed and/or ribbed. The advantage of such a construction resides in the distinctly lower weight and in the enhanced air supply, whereby the stability and inherent rigidity of the shell-like members can be increased by means of a pertinent lattice or rib structure.

According to the invention, the lattice stays and/or ribs are comprised of longitudinal and transversal ribs, while the lattice straps or ribs possess an expedient diameter ranging between 1.5 cm and 3 cm.

It is possible to achieve a particularly good inherent rigidity when at least one longitudinal rib per shell portion is provided, which extends substantially across the entire length of the shell portion and which is constructed so as to be at least as wide or possessing a larger cross-section than the other longitudinal stays, transversal stays or ribs. So far as the L-shaped shell portions are not constructed in a single piece, but are multi sectional, this will accordingly also apply to the individual components. By preference, the lattice stays and/or the ribs, in each case, in dependence of the loads or stresses acting upon them, are provided with differing widths and/or possessing a different diameter. It is possible to hereby functionally adapt the shell portion, in which case the thickest longitudinal or transversal ribs or stays are employed only where the load or stress is greatest but are, in other areas, dimensioned so as to be weaker. It is possible to hereby optimize the saving in weight. In order to also render the transition from the more robust longitudinal ribs extending over the entire length to the weaker transversal ribs in a manner which is more resistant to fracture or rupture, the attachment portions of the transversal ribs to the longitudinal ribs are wider than the following transversal rib portion preferably constructed in the width or in the diameter so as to be tapering.

According to another construction of the invention, at least the posterior leg portion of the shell-like member possesses a longitudinal slot for the adjustment of the width or the diameter, whereby one and the same shell-like member can be adapted to the individual calf configuration of the patient. The longitudinal ribs framing the longitudinal slot are adjustable and can be fixated by means of a detachable connecting element to the desired spacing, whereby a constructionally simple solution has been found.

According to another construction of the invention, the anterior shell portion possesses a foot portion which is swivellable relative to its leg portion by means of a hinge. This applies analogously to the posterior shell portion. With this it is made possible to be able to adjust or set desired swivel angles. In the event that the foot is to be immobilized relative to the lower leg in a fixed angular position, provision is additionally made for the hinge and/or the second hinge to be locked in any desired position.

Another embodiment of the invention consists in that the foot portion, which is adjustable relative to the leg portion of the anterior shell-like member of the fixation means, is connected by means of a section configured in the manner of an accordion or concertina bellows with a plurality of folded, film hinge-like constructed and interconnected strips of material, in which the swivel hinges that interconnect the foot portion and the leg portion and are constructed laterally on the shell-like member are provided with angle locking means. The swivellability and thus the angle variability of the foot portion relative to the leg portion is brought about by the help of film hinges that are disposed parallelly to each other, in which case the fixation of the foot portion relative to the leg portion in the angular positions of 90° and 120° is then effected by means of the swivel hinges. The hinges area between the foot portion and the leg portion of the anterior shell-like member is achieved by means of a material section which makes variability in width possible.

In a preferred embodiment, the angular adjustment means for adjusting the foot portion relative to the leg portion of the anterior shell portion is comprised of the plate-shaped angle adapter, disposed between the foot portion and the leg portion of the anterior shell portion, and configured corresponding to the external contour of the shell-like member or the anterior shell portion, and said angle adapter is detachably retained by means of click-stop and locking means on the leg portion and the foot portion. This plate-shaped angle adapter, in accordance with one embodiment, possesses a width, by virtue of which the foot portion assumes an angular position of 90° relative to the leg portion of the anterior shell portion so that, with the angle adapter inserted, the foot portion is at an angle of 90° relative to the leg portion. According to another embodiment, the plate-shaped angle adapter possesses a width, by virtue of which the foot portion assumes an angular position of 120° relative to the leg portion of the anterior shell portion. In this manner it is possible to obtain the normal angular position of the foot relative to the lower hinge, viz. the angular position of 90°, whereas, in the disposition of a wider angle adapter, the pes equinus position of the foot relative to the lower leg of 120° can be adjusted and obtained.

For the employment of differently dimensioned angle adapters within the area connecting the foot portion to the leg portion there is a window-like perforation which extends into the lateral area of the foot portion and the leg portion so that the plate-shaped angle adapter inserted into the window-like perforation bridges the open area between the foot portion and the leg portion, whereby the requisite angular position of the foot portion relative to the leg portion is obtained.

The attachment of the angle adapter is preferably effected with the aid of stationary and rotatable locking hooks and by the use of contoured marginal areas, in which case the rotatable locking hooks are constructed in the form of eccentrics so that, through the locking hooks, the angle adapter is clamped or stretched across the foot portion and the leg portion of the anterior shell portion, whereby a press fit free from play is obtained. In this manner it is possible, by employing the pertinently constructed angle adapter, to effortlessly obtain one or the other required angular position.

On the strength of constructing the fixation device according to the invention it is possible, in a shell-like member comprised of two reciprocally tightenable shell portions, to adapt the anterior shell portion in which the foot portion, relative to the leg portion, is intended to assume a predetermined, non-variable angular position to the requisite angular position predetermined by the posterior shell portion. According to this, the anterior shell portion comprises the leg portion, the foot portion and the angle adapter insertable between the two components, whereby it is possible to readjust or reset the fixation device from a pes equinus position—angular position of 120°—to the normal position—angular position of 90°.

Consequently, an adaptability of the anterior shell portion to the posterior shell portion does exist. In the present case merely two types of angle adapters are required, viz. an angle adapter which makes the adjustment or setting of an angle of 90° possible and an angle adapter which makes an adjustment or setting to 120° possible.

With all the constructions according to the invention the advantage is achieved that also positional changes, such as angular changes of the foot portion, are effortlessly possible subsequent to a certain period of treatment. Consequently, the most widely varying angular positions can be fixated in the simplest fashion which, with regard to the known plaster casts or bandages, is particularly advantageous in so far as the known plaster casts are only capable of assuming one or the other angular position since, after the plaster has set, no angular changes of the foot portion can be effected.

The invention also provides that at least the posterior top leg portion of the shell-like member possesses at least one longitudinal slot for the adjustment of the width and of the diameter. By means of this simple constructional step, an adjustment of the distance or spacing is possible and, with it, an individual adaptation to the diameter of the extremity.

According to an improvement of the invention, guideways framing the longitudinal slot are adjustable to the desired spacing with the aid of a detachable connecting element and can be fixated. This embodiment possesses the advantage that, depending upon the disposition of the guideways and the relative position of the detachable collecting element, a continuous adjustment of the diameter of the top leg portion can be achieved. The guideways may, by way of example, be disposed in such a way that they diverge at an acute or obtuse angle so that, when the connecting element is moved longitudinally along the guideways, different longitudinal slot spacings in the top leg portion can be set.

For reasons related to manufacturing engineering, the connecting element can be a sliding member possessing marginal contours which partially engage into the circumference or marginal contouring engaging into the guideways.

In order to be able to optionally employ the diameter adjustment or to abstain from making use of the same, according to another embodiment of the invention, one of the two guideways projects over the other in the direction of the longitudinal axis of the shell portion by a length which is at least as great as the length of the sliding member or of the connecting element. By arranging the connecting element at the level of the projecting part, it is possible for the connecting element to be secured (on one side) without it being in engagement with the second guideway. The handleability of the connecting element is improved hereby since it only has to be pushed over the second guideway for changing the spacing. By preference one of the guideways is essentially constructed up to the top shell portion margin.

In order to prevent the loss of the detachable connecting element or of the sliding member, a limit stop delimits the displaceability in the direction of the top leg portion rim. In this case, the connecting element or the sliding member is secured against being inadvertently pulled off the longer guideway.

In a concrete embodiment, the top leg portion possesses two rib-like or bead-like raised portions that proceed substantially parallel to each other, and which engage into correspondingly configured grooves of the sliding member, which is longitudinally displaceable but secured against being laterally removed. More particularly, the guideway may possess a dovetail construction.

For weight saving purposes, but also to improve the air supply to the ensheathed extremity regions, the wall areas of the shell-like member are, at least in part, constructed so as to be latticed and/or ribbed. On this occasion, it is preferably possible to employ two longitudinal ribs of the top leg portion for the purpose of utilizing the same as sliding member guideways.

According to another embodiment of the invention, the fixation device is constructed in such a way that, of the two shell portions possessing an approximately L-shaped configuration with an approximately semicircular cross-section and having a leg portion as well as foot portion, the posterior shell portion posesses a foot portion that is adjustable to the leg portion angle of the same. Within the band or strap area located opposite the foot portion, a window-like perforation with an interchangeable plate-shaped angle adapter is inserted therein, which is provided with an engagement aperture into which a pin engages for fixating the angle between the foot portion and the leg portion of the anterior shell portion, said pin being formed onto the foot portion of the anterior shell portion for the fixation of a predetermined angular position.

Since the posterior shell portion of the shell-like member of the fixation device is constructed for the accommodation of a plate-shaped angle adapter, in connection with the pin disposed on the foot portion of the posterior shell portion the possibility exists for disposing the foot portion in relation to the leg portion in the requisite angular position, to fixate and to retain the same. In this case the angular position of the foot portion is predetermined by the position and disposition of the engagement aperture in the plate-shaped angle adapter. If the engagement aperture is provided within the lower area of the angle adapter and the pins of the foot portions engage into the positionally preset engagement aperture, the normal angular position of the foot relative to the lower hinge, viz. the angular position of 90° is obtained. However, when the engagement aperture for the pins is within the upper area of the angle adapter, the pes equinus position of 120° of the foot relative to the lower leg is obtained. If, on the other hand, the plate-shaped angle adapter is provided with a slot-like engagement aperture extending approximately over the entire length of the angle adapter, then it is possible to adjust or set the most widely varying angular positions of the foot relative to the lower leg of the patient. If, over and above that, the pin formed onto the foot portion is provided with a setscrew, then there is a possibility of fixating the foot portion set to a certain angular position in the direction of the leg portion of the device.

Owing to the circumstance that, in the wall of the posterior leg portion, the plate-shaped angle adapter is retained in a window-like perforation expediently by means of a clamping fit, an effortless interchange of angle adapters with the most widely varying arrangements and positions of the engagement apertures is possible. The further advantage consists in that also positional changes, i.e. angular changes in the foot position, are effortlessly possible after a certain period of treatment. Consequently, the most widely varying angular positions can be locked in the simplest fashion which, relative to the known plaster casts or bandages, is particularly advantageous since the known plaster casts take into account only one or the other angular position as, after the setting of the plaster, no angular changes of the foot portion can be effected any longer once the plaster is set.

The fixation device is constructed in such a way that of the two shell portions possessing an approximate L-shape with an approximately semicircular cross-section and having a leg portion and a foot portion, the anterior shell portion possesses a foot portion which is angularly adjustable to the leg portion of the same and, within the area between the foot portion and the leg portion, possesses an angle setting means. With the aid of the angle setting means the foot portion can, relative to the leg portion, be locked in a predetermined angular position, in which case the posterior shell portion has a foot portion which is angularly adjustable to the leg portion of the same or a foot portion locked at a predetermined angle to the leg portion.

Due to the circumstance that the anterior shell portion of the shell-like member of the fixation device, for the accommodation of a plate-shaped angle adapter, is constructed in the form of an angle adjustment or setting means, the possibility exists for disposing the foot portion relative to the leg portion in the requisite angular position and to thus secure the foot portion relative to the leg portion at the necessary angle, which is predetermined by the position and disposition and the dimensions of the angle adapter.

In a preferred embodiment, the angle adjustment or setting means for the foot portion relative to the leg portion of the anterior shell portion of the shell-like member of the fixation device comprises of the plate-shaped angle adapter disposed between the foot portion and the leg portion and contoured in correspondence to the external outline of the shell-like member or the anterior shell portion. The angle adapter is detachably retained with the aid of clickstop and locking means on the leg portion and the foot portion of the anterior shell portion. According to an embodiment, this plate-shaped angle adapter possesses a width, by virtue of which the foot portion, relative to the leg portion of the anterior shell portion, assumes an angular position of 90° so that, when the angle adapter is inserted, the foot portion is disposed at an angle of 90° relative to the leg portion. According to a further embodiment, the plate-shaped angle adapter possesses a width, by virtue of which the foot portion, relative to the leg portion of the anterior shell portion, assumes an angular position of 120°. In this fashion it is possible to obtain the normal angular position of the foot relative to the bottom hinge, viz. the angular position of 90°, whereas, with the disposition of a wider angle adapter, the pes equinus position of 120° of the foot in relation to the lower leg can be adjusted and obtained.

For the employment of differently dimensioned angle adapters within the connecting area from the foot portion to the leg portion, the foot portion and the leg portion of the anterior shell member possess a window-like perforation which extends as far into the lateral area of the foot portion and the leg portion. The plate-shaped angle adapter inserted into the window-like perforation bridges this open area between the foot portion and the leg portion, whereby the angular position of the foot portion relative to the leg portion is obtained.

The mounting of the angle adapter is preferably effected with the aid of stationary and rotatable locking hooks and by using contoured marginal areas. The rotatable locking hooks are constructed on the form of eccentrics so that, by means of the rotatable, eccentrically constructed locking hooks, the angle adapter is clamped across the foot portion and the leg portion of the anterior shell portion, whereby a force fit free from play is achieved. In this way, it is possible to effortlessly achieve one or the other requisite angular position by employing the pertinently constructed angle adapter.

By virtue of this construction of the fixation device it is possible, in a shell-like member comprising two reciprocally tightenable shell portions, to also adapt the anterior shell portion in which the foot portion is intended to assume, relative to the leg portion, a predetermined, non-variable angular position, to the required angular position and thus to the angular position predetermined by the posterior shell portion. Accordingly, the anterior shell portion is comprised of the leg portion, the foot portion and the angle adapter inserted between the two components, whereby the possibility exists of readjusting from a pes equinus position—angular position 120°—the fixation device to the normal angular position of 90°. Thus, an adaptability of the anterior shell portion to the posterior shell portion exists. In the present case, merely two angle adapter types are required, viz. on the one hand, an angle adapter which makes an adjustment of the angle to 90° possible and, on the other, an angle adapter which makes an adjustment to 120° possible.

A further embodiment consists in that the foot portion, which is adjustable relative to the leg portion of the anterior shell portion of the shell-like member, is connected by means of an accordeon bellows-like constructed section proceeding transversally to the leg portion's longitudinal direction. The accordeon bellows-like constructed section is provided with a plurality of folded, film hinge-like configured and interconnected strips of material, in which case the swivel hinges that interconnect the foot portion and the leg portion formed laterally on the shell-like member are provided with angle locking means. The swivellability and thus the angular variability of the foot portion relative to the leg portion is achieved with the aid of a large number of film hinges disposed so as to be parallel to each other, in which case the locking of the foot portion relative to the leg portion is effected in the angular positions of 90° and 120° by means of the swivel hinges. The hinge area between the foot portion and the leg portion of the anterior shell portion is achieved by means of a material section which makes a variability in width possible.

With all these constructions the disadvantage is achieved that also positional changes, i.e. angular variations of the foot portion after a certain treatment period are effortlessly possible. It is, therefore, possible to fixate the most widely varied angular positions in the simplest manner which, in comparison with the known plaster casts, is especially advantageous in so far as the known plaster casts are able to assume a fixed position since, once the plaster has set, it is not possible to make any angular changes of the foot portion.

A good adaptation to the respective calf of the patient is achieved with a fixation device comprising of two shell portions possessing an L-like configuration that are reciprocally tightenable so as to constitute a shell-like member and which possess an approximately semicircular cross-section so that the lower leg of the patient is engaged around by sections from both sides with the aid of the two shell portions. The posterior shell portion possesses, while forming at least one section which can be bent aside and setting out from the upper leg portion rim, slot-like perforations which extend across an area in the longitudinal direction of the shell portion in such a way that, in the posterior shell portion, springably elastic and mutually displaceable wall sections are formed. These sections can be fixated or tightened with the aid of a means so that a high degree of inherent stability together with a high degree of accuracy of fit is achieved.

Owing to the circumstance that the posterior shell portion of the shell-like member possesses, while forming at least one section which can be bent aside and setting out from the upper shell portion rim, slot-shaped perforations which extend across an area in the direction of the shell portion longitudinal direction in such a way that springably elastic and reciprocally displaceable wall sections are formed. These sections can be fixated or tightened with the aid of a means so that a high degree of inherent stability together with a high degree of accuracy of fit is achieved.

Due to the circumstance that the posterior shell portion of the shell-like member possesses reciprocally displaceable, springably elastic wall sections, this shell portion is adaptable to every calf size and dimension so that a positional fixation of the lower leg of the patient in a shell-like member is ensured, while retaining the normal angular position between foot and lower leg. The means for fixating the reciprocally displaceable and springably elastic wall sections of the posterior shell portion may be constructed in the form of a tightening strap. It is possible, however, to employ otherwise constructed fixation means, such as clamping means and suchlike. It is essential that, in adaptation to the respective calf configuration and calf size of the lower leg of the patient, the shell portions of the shell-like member are fixated in such a way that not merely a stabilization within the posterior region, but also a lateral stabilization is obtained. In addition, the section which can be bent aside in the wall of the posterior shell portion acts, when a calf muscle is moved, in the form of a muscle pump acting upon the calf, whereby a thrombosis prophylaxis is achieved. When the anterior shell portion is mounted upon the posterior shell portion, the anterior shell portion predetermines the 90° angle for the posterior shell portion and, consequently, for the position of the foot relative to the lower leg. The lateral wall sections of the posterior shell portion are stationary and act as stabilizers in the process, which is particularly advantageous when no anterior covering, and, therefore, no anterior shell portion, is provided. In the case of a lacking anterior shell portion, the closing elements engage on the stationary wall sections of the posterior shell portion. The anterior shell portion serves as the stabilizer and predetermines the 90° angle.

Further advantageous constructions according to the invention form the subject matter of the subclaims.

BRIEF DESCRIPTION OF THE DRAWINGS

Embodiment examples of the invention are explained in greater detail below with the aid of the drawings. Thus FIGS. 1 and 2 each show different embodiments of the invention in a perspective view;

FIG. 41 shows a rear view of the posterior shell portion.

DETAILED DESCRIPTION OF THE INVENTION

Figure 1:
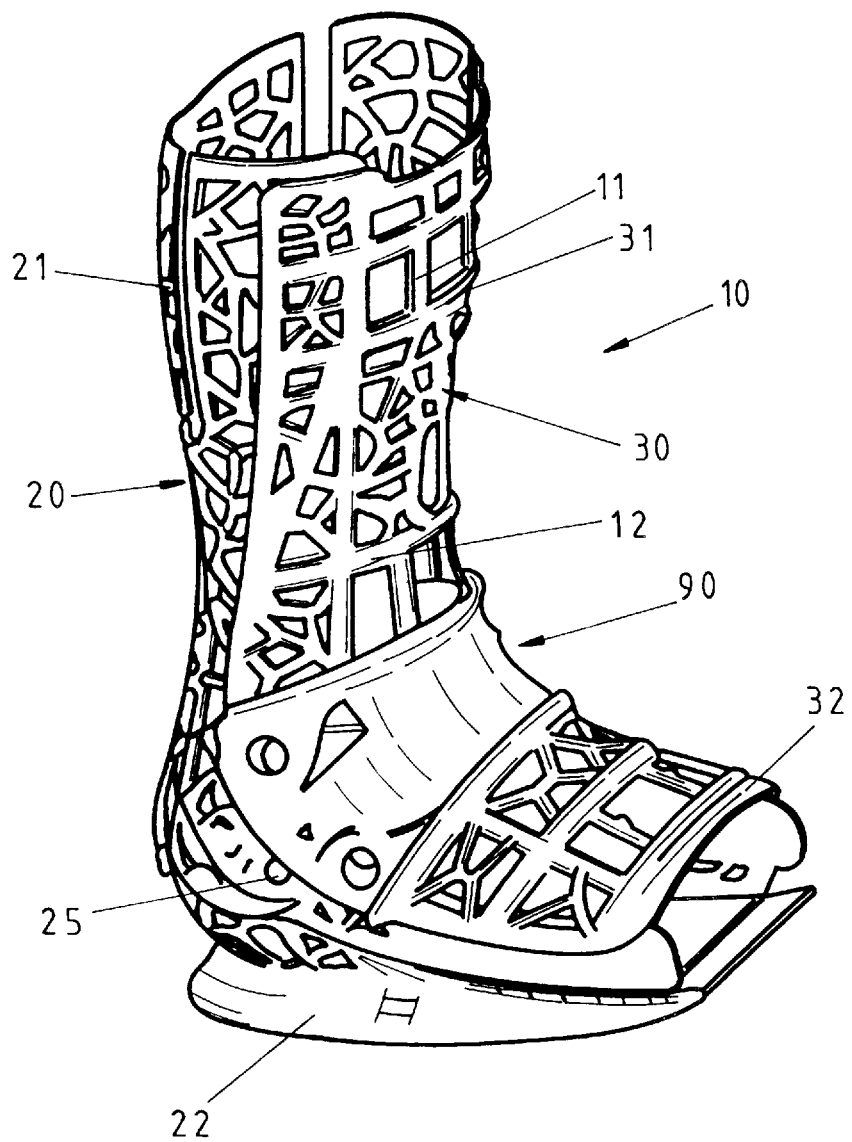
Figure 2:
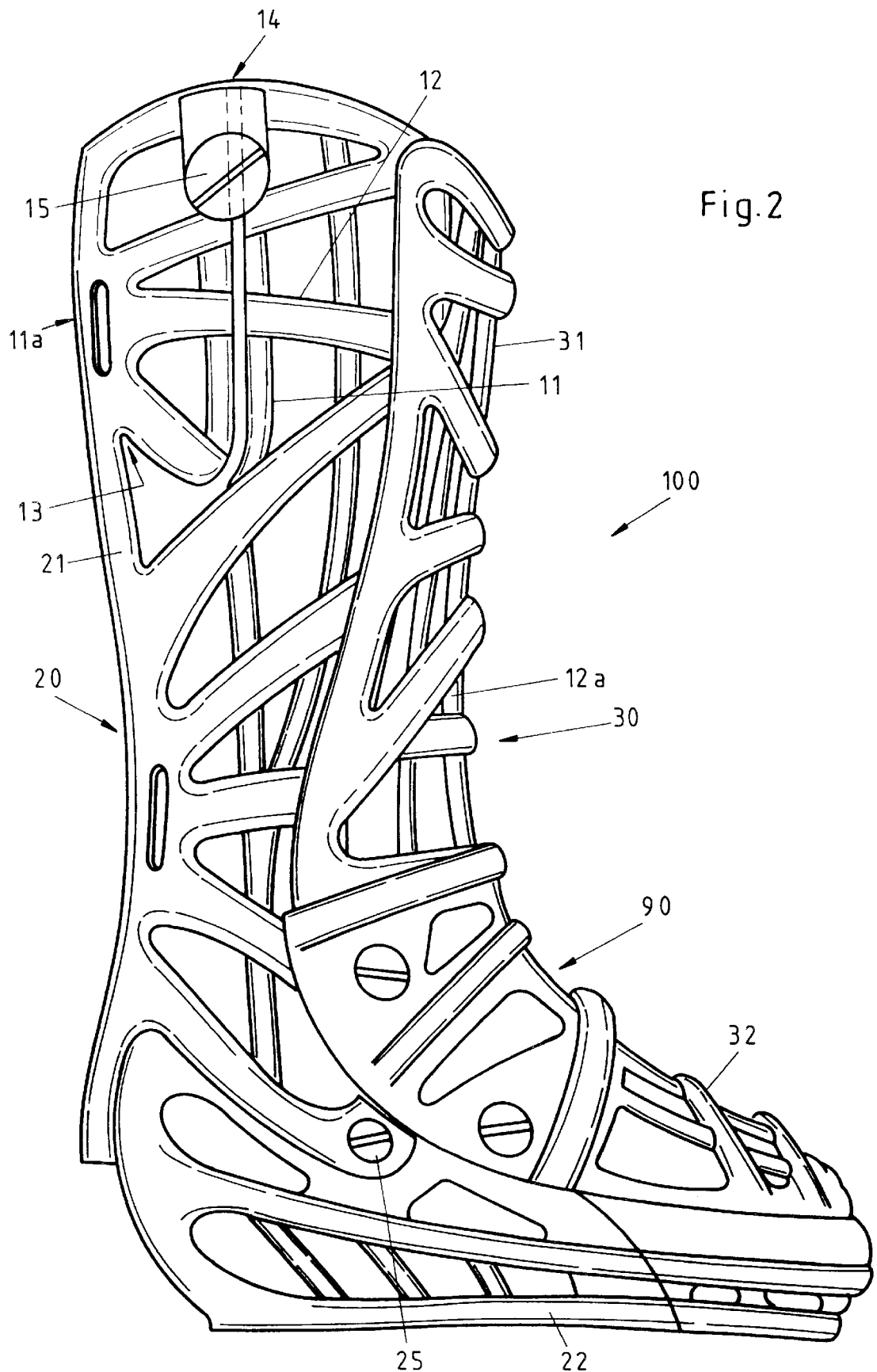

A device for the ensheathing fixation of extremities is depicted in the FIGS. 1 and 2 in the form of a shell-like member 10 for the foot/lower leg region of a patient. The shell-like member 10 is comprised of two reciprocally tightenable shell portions, viz. a posterior shell portion 20 and an anterior shell portion 30, in which case both shell portions 20, 30 possess an approximately L-shaped configuration. Each shell portion 20 or 30 is comprised of a leg portion 21 or 31 and a foot portion 22 or 32, in which case the foot portions 22, 32 are interconnected with their leg portions 21, 31 by means of lateral swivel hinges 25, 35 so that the foot portions 22, 32 are swivellable relative to the leg portions 21, 31 about swivel axes 25a, 35a. Both two shell portions as well as their swivel hinges are expediently comprised of plastic.

The foot portions 22, 32 and the leg portions 21, 31 of the shell portions are constructed in a shell-like fashion, and to be open on one side, in the posterior shell portion 20, an accommodation trough for the foot and the lower leg is provided. The anterior shell-like member 30 is also constructed in the same manner so that it, with its leg portion 31 and its foot portion 32, is attachable to the leg portion 21 and the foot portion 22 of the posterior shell portion 20. On the underside of the foot portion 22 of the posterior shell portion 20, an outsole 23 is provided whose external construction is adapted to the rolling movement of the foot when walking. For this the outsole 23 is constructed in the form of a walking rocker or provided with a walking support 24.

Figure 5:
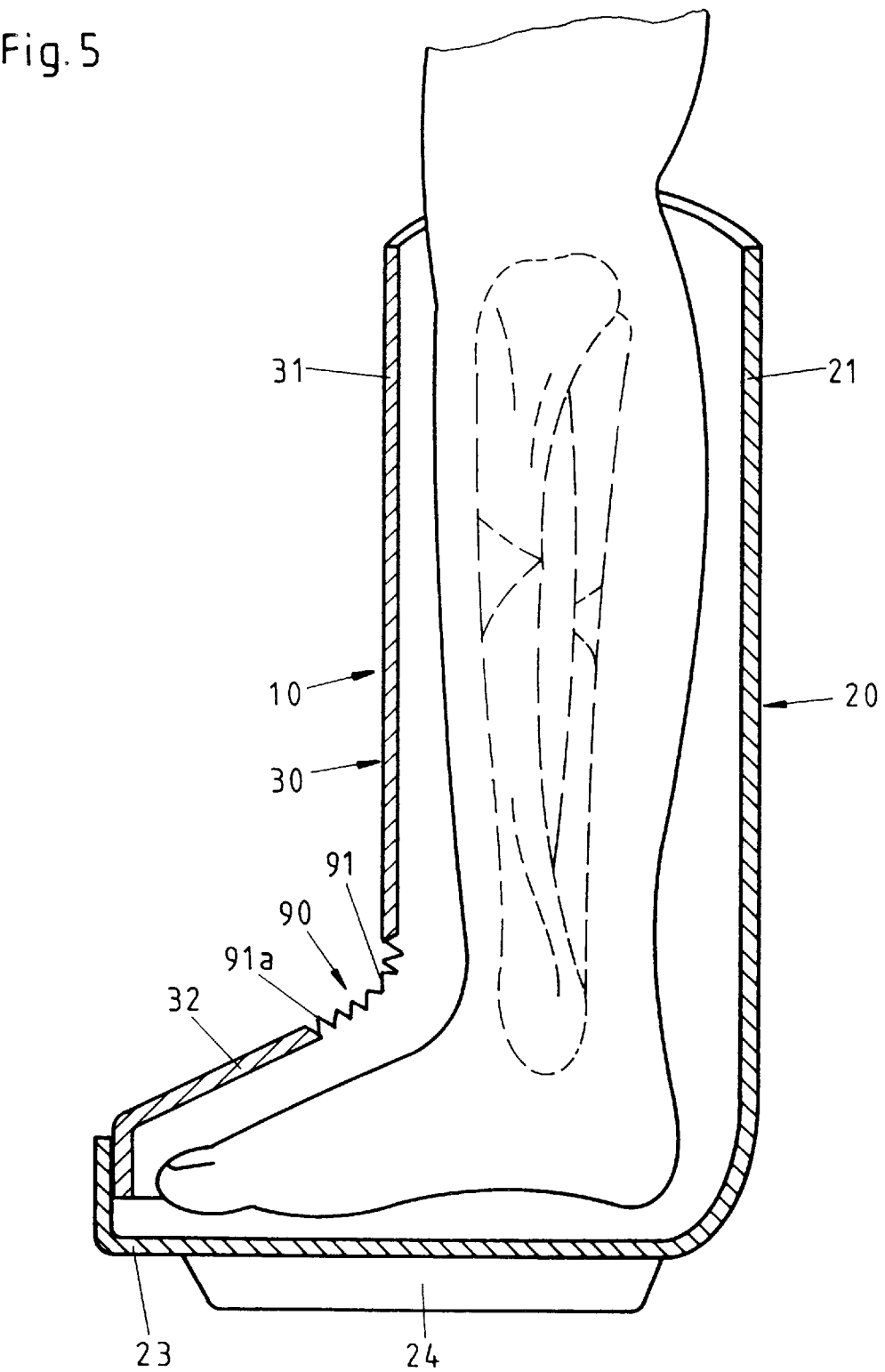
FIG. 5 shows the fixation device according to FIG. 4, partly in a side view and partly in a vertical longitudinal section.
Figure 6:
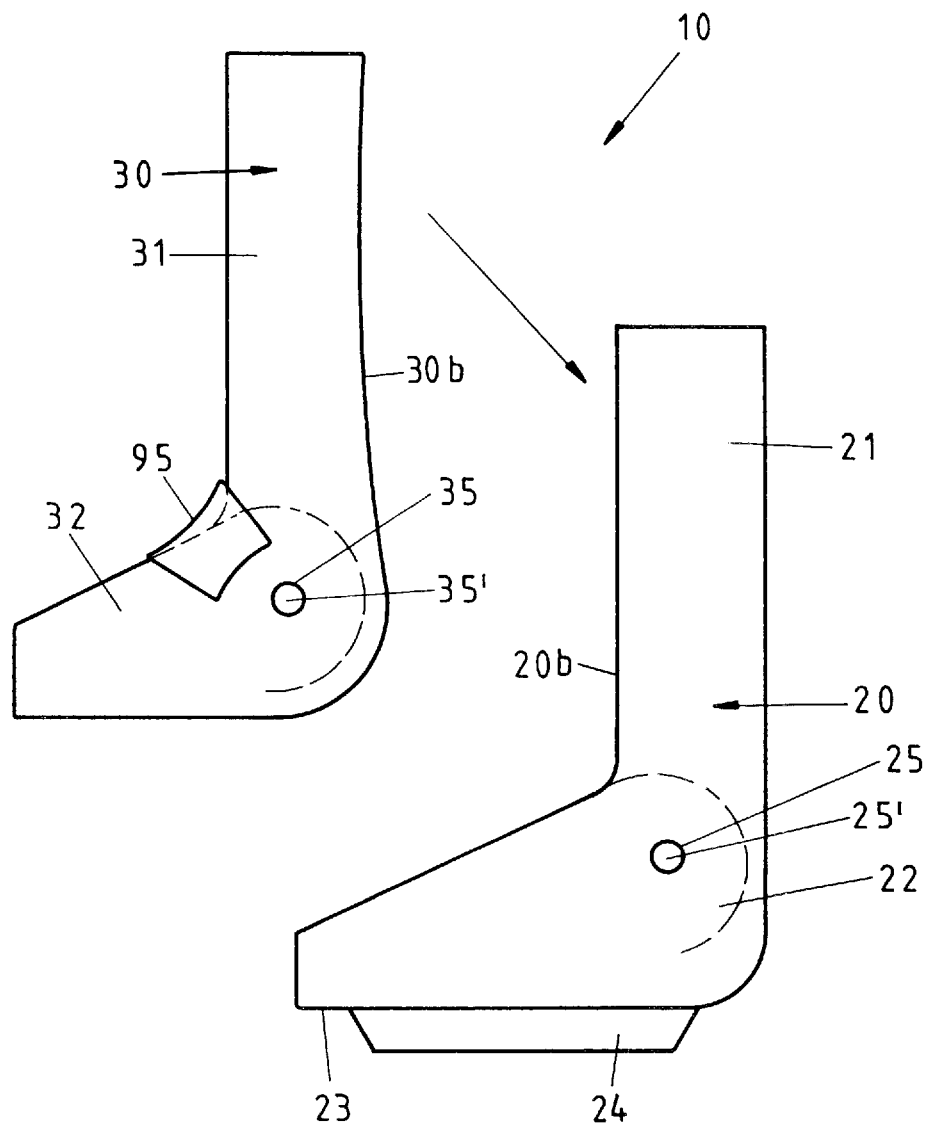
FIG. 6 shows in a side view the two L-shaped shell portions of the shell-like member prior to their being tightened.

The foot portions 22, 23 and the leg portions 21, 31 of the two shell portions 20, 30 of the shell-like member 10 are, in the direction towards the foot, constructed in a shell-like fashion. In this case, the construction is such that the anterior shell portion 30 is insertable into the posterior shell portion 20 in such a way that the lateral wall sections of the posterior shell portion 20 engage over the lateral wall sections of the shell portion 30 in a section-wise manner (FIG. 5).

Both the shell portion 20 as well as the shell portion 30 possess an approximately semicircular cross-section so that, when the shell portions are placed on top of each other, a section-wise engagement over the side wall section of the two shell portions 20, 30 takes place. In order to be able to engage laterally around the lower leg and also the foot, the shell portions 20, 30 possess a certain elasticity. The elasticity of the side walls of the two shell portions 20, 30 expediently increases from their central areas of the leg portions to their free anterior rims of each shell portion.

The difference between the embodiment illustrated in the FIG. 1 and the one according to FIG. 2 resides in that, in FIG. 1, the shell portions 20, 30 possess a (more close-meshed) lattice structure than is brought about by the ribs 11, 12. On this occasion the longitudinal ribs are identified with 11 and the transversal ribs with 12, in which case the leg portions 21 and 31 of the posterior shell portion 20 and the anterior shell portion 30 each possess a continuous longitudinal rib 11a and 12a, which are constructed to be sturdier than the transverse ribs 12 and the remaining longitudinal ribs. At the attachment points 13 between the continuous longitudinal ribs 11a and the transversal ribs, the transitional area is constructed so as to be wider or larger in diameter. With regard to the structure, which can be achieved by means of longitudinal ribs 11 and transversal ribs 12 including obliquely proceeding ribs, no fixed contours are required for as long as the requisite inherent rigidity and strength or bending strength of the shell portions is achieved. At any rate, the essential concept of the invention is that a considerable amount of material can be saved by a latticed or ribbed construction and, over and above that, the air supply is enhanced.

Furthermore, in the upper leg portion 21, two longitudinal ribs in a side-by-side arrangement are provided which form a gap 14 that is bridged by a connecting means 15. In its width, the gap 14 is variable so that the leg portion can be adapted to the calves of the patients. It is also possible for the posterior shell portion 20 to be employed on its own for the fixation of an extremity which, with the aid of bands or the like, is retained and fixated in the shell portion.

Between the two reciprocally tightenable shell portions 20, 30 and the extremity, at least one deformable, vacuum-tight-constructed padding is provided with at least one valve that is comprised of a bladder, in which a great number of small filling material particles are provided which are movable in relation to each other (not depicted in the drawing). The padding, which can be applied tightly so as to fit well to the limb section to be treated during evacuations that are effected within a short time, becomes hard and inherently stable in the configuration created during the application operation. In conjunction with the hard shell portions, a very sturdy sleeve is produced which is well modeled onto the extremity in question and which does not give rise to any pressure sores since, during the consolidation of this object, no radial, inwardly directed pressure is generated and no edges or projections can be formed on the inside either. In lieu of such a sleeve-like padding, it is also possible to make use of a pad of some suitable material, or to employ a sock pulled over the foot and lower leg.

The closing elements expediently provided on the longitudinal marginal areas of the foot portion and the leg portion (not shown in the drawing), and which are in particular comprised of pieces of Velcro strip fasteners, do provide very simply and speedily the slight bearing pressure of the padding on the closed shell-like member. The bearing pressure is necessary prior to the evacuation being carried out. In this mode it is possible to produce a sleeve possessing an absolutely correct fit and to fixate it with the aid of the Velcro strip fastener. After the evacuation has been performed, a sleeve is available which is consolidated in itself and stabilized in its configuration and which retains the extremity in a positionally secure manner.

It is possible to prevent an ankle movement by the patient by firmly setting the angle of inclination of the leg portion relative to the foot portion about the swivel axis 25 or 35. A selection of this firmly set angle can be made in dependence of the injury to be treated within the entire adjustable swivel angle range. The fixation at a specific angle is effected with the aid of pertinently constructed adjusting means. In this connection, in the posterior leg portion 20, an angular presetting for setting an angle of 90° or 120° between the foot portion 22 and the leg portion 21 can take place with the aid of an angle adapter that is not depicted in the drawing.

In order to be able to effect an adaptation of the anterior shell portion 30 to the angular position of the foot portion 22 relative to the leg portion 21 of the posterior shell portion 20, the anterior shell portion 30 is provided with an angle adjusting means 90, with the aid of which the foot portion 32 can be locked relative to the leg portion 31 in a predetermined angular position. The angular position then coincides with the angular position of the foot portion 22, relative to the leg portion 21 of the posterior shell portion 20.

Figure 3:
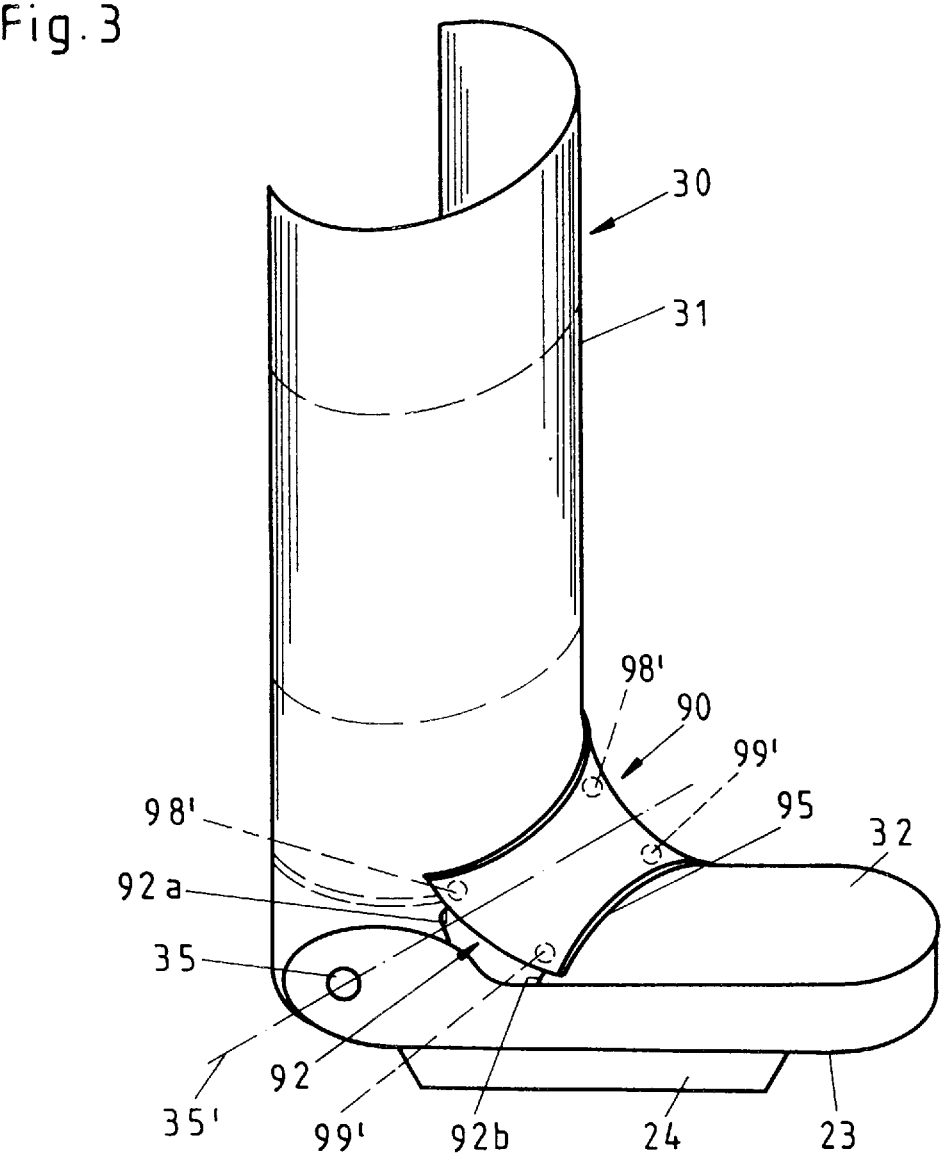
FIG. 3 shows a schematic, diagrammatical view of the anterior shell portion of the fixation device, comprising two L-shaped shell portions with an inserted angle adapter.
Figure 4:
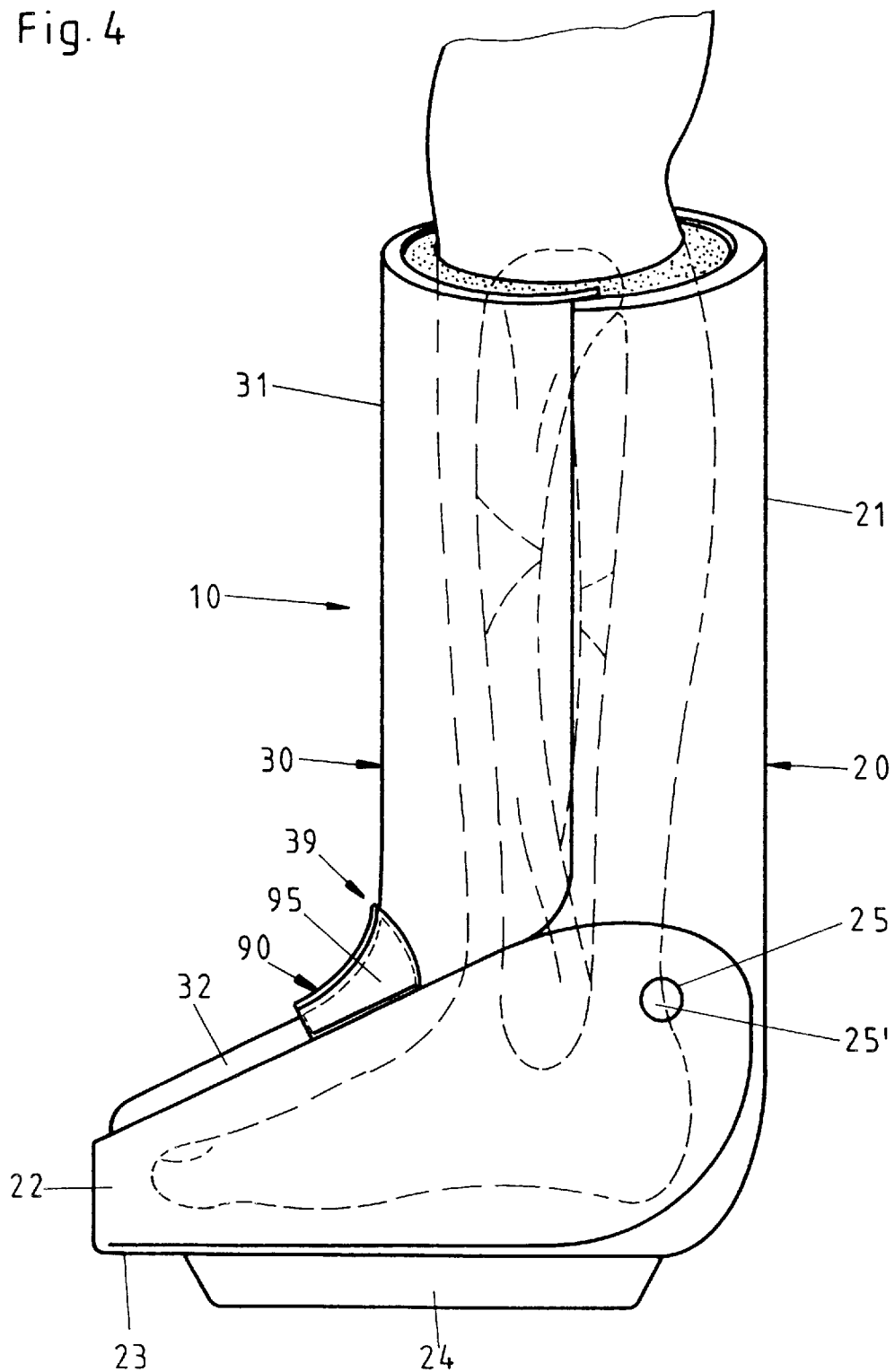
FIG. 4 shows a side view of the fixation device comprising a shell-like member with two L-shaped shell portions.
Figure 7:
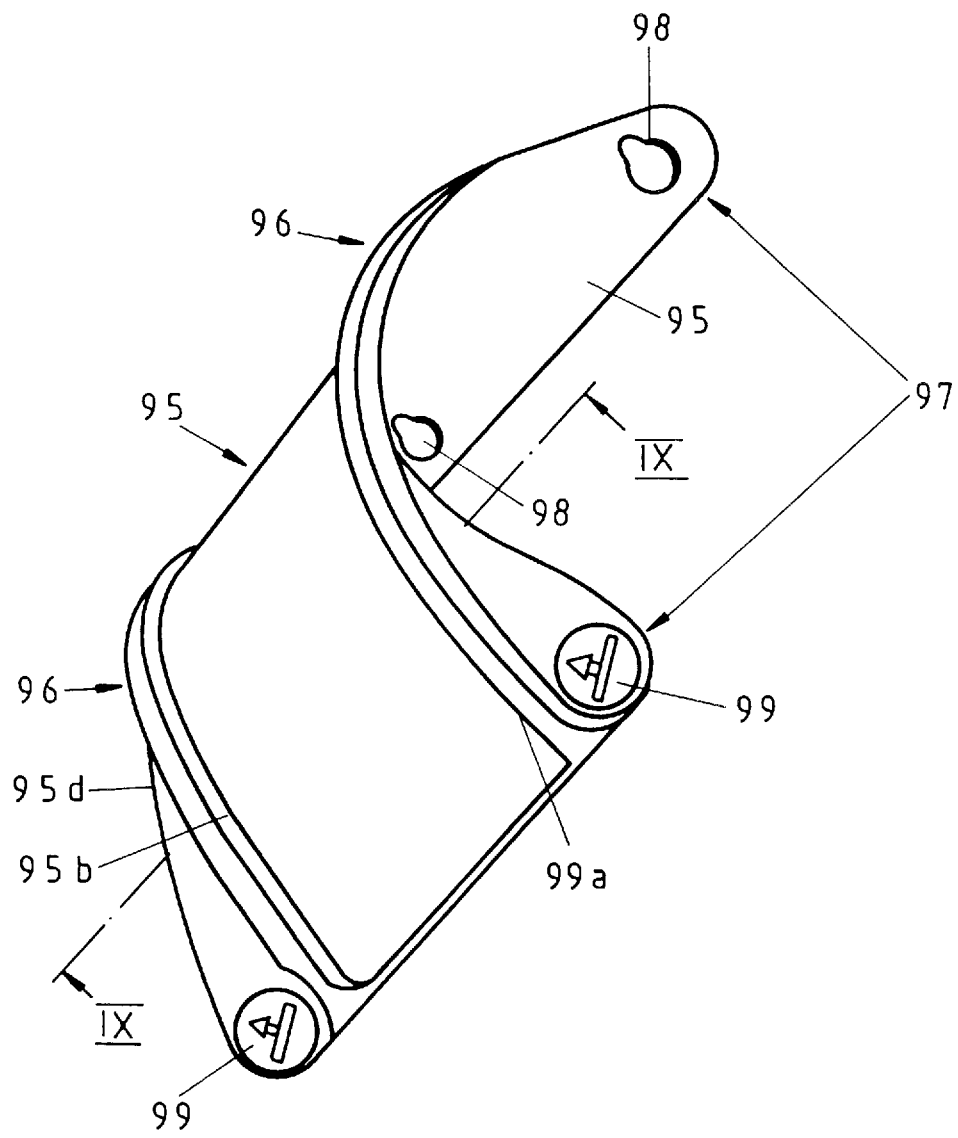
FIG. 7 shows in a diagrammatical view an angle adapter for an angular position of 90° between the foot portion and the leg portion of the anterior shell portion.

This angle adjusting means 90 is comprised of a plate-shaped angle adapter 95 that is disposed between the foot portion 32 and the leg portion 31 of the anterior shell portion 30 and configured to correspond to the external contour of the shell-like member 10 or of the anterior shell portion 30. The said angle adapter is detachably retained with the aid of click-stop and locking means 97 on the leg portion 31 and the foot portion 32 of the anterior shell portion 30 (FIGS. 3 and 7). This angle adapter 95 engages in a lug-like fashion on the front side over the connecting area 39 between the foot portion 32 and the leg portion 31 of the anterior shell portion 30.

This plate-shaped angle adapter 95 possesses a width, by virtue of which the foot portion 32 assumes, relative to the leg portion 31 of the shell portion 30, an angular position of 90° (FIG. 7). This angular position is the normal position between the foot and the lower leg.

Figure 8:
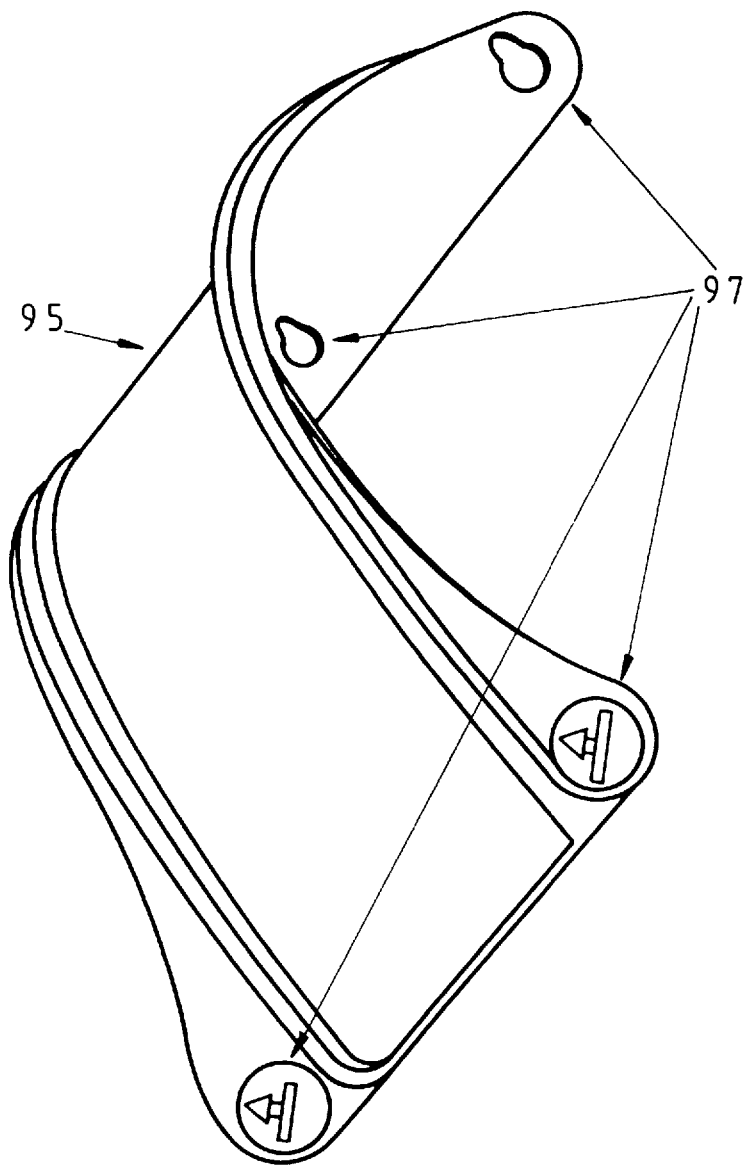
FIG. 8 shows a diagrammatical view of an angle adapter for an angular position of 120° between the foot portion and the leg portion of the anterior shell portion.

A further embodiment of the angle adapter 95 makes provision for a width, by virtue of which the foot portion 32 assumes, relative to the leg portion 31 of the shell portion 30, an angular position of 120°. When this embodiment of the angle adapter is inserted between the foot portion 32 and the leg portion 31 of the shell portion 30, the foot portion 32, relative to the leg portion 31, assumes the pes equinus angular position (FIG. 8).

The foot portion 32 and the leg portion 31 of the anterior shell portion 30, within the connecting area 39 of these two components, possesses a window-like perforation 92 that extends as far as approximately into the lateral area of the foot portion 32 and the leg portion 31. Because of this, the angle adapter 95 attached to the shell portion 30, engages over this window-like perforation 92 in the form of a covering lug, in which case the dimensions of the angle adapter 95 are selected in such a way that it is insertable into the window-like perforation 321 or, with its circumferential rim, is attachable onto the rim which delimits the window-like perforation 92 and is retained there by means of clamping or force fit.

Figure 9:
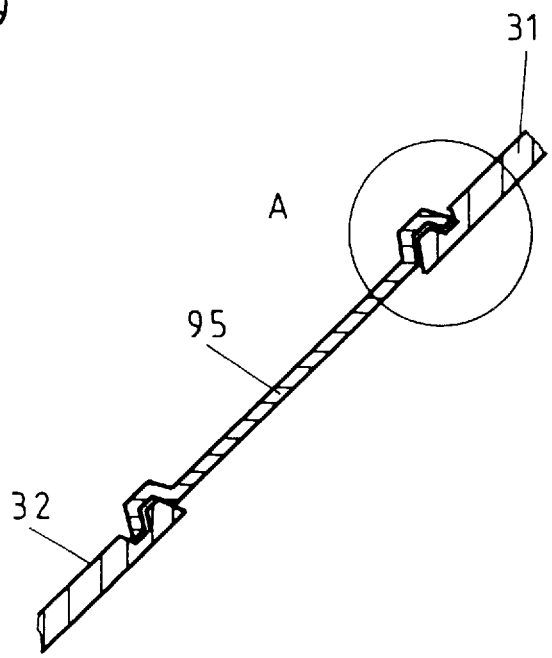
FIG. 9 shows a section in the direction of Line IX—IX in FIG. 7.

In order to mount the angle adapter 95 on the wall areas of the foot portion 32 and of the leg portion 31 of the shell portion 30, the oppositely located rims 92a, 92b proceeding transversally to the longitudinal direction of the leg portion of the window-like perforation 92 are provided on the outside with bead-like or otherwise configured, strip-like reinforcements 93. Meanwhile, the angle adapter 95, on its upper rim 95a and on its lower rim 95b with the reinforcements 93 on the rims 92a, 92b, is provided with pertinently constructed mating or counter contours in the form of marginal contours 96 so that the angle adapter 95 is retained by means of clamping force on the reinforcements 93 on the foot portion 32 or the leg portion 31 or on those of the anterior shell portion 30 (FIG. 9).

Figure 10:
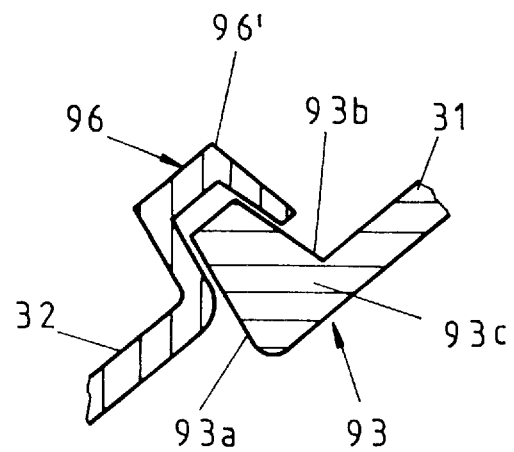
FIG. 10 shows, in an enlarged reproduction, the connecting section A between the angle adapter and the wall area of the leg portion of the anterior shell portion.

The marginal reinforcements 93 on the foot portion 32 and on the leg portion 31 of the anterior shell portion 30 possess a cross-section having a surface area 93c with square or rectangular, conically upwardly proceeding lateral surfaces 93a, 93b (FIG. 10). The marginal contours 96 on the plate-shaped angle adapter 95 are constructed in the form of a corresponding, matching or counter contour 96' engaging over the marginal reinforcement 93 on foot portion 32 and the leg portion 31.

The attachment and mounting of the angle adapter 95 to the leg portion 31 and the foot portion 32 of the anterior shell portion 30 is, according to FIG. 7, effected with the aid of two locking hooks 98 stationarily disposed on the one end 95c of the angle adapter. These hooks engage into perforations 98' in the wall areas of the leg portion 31 and of the foot portion 32 of the shell portion 30. The angle adapter 95 is hooked with this one end 95c into the perforations 98' that are provided in the wall areas of the leg portion 31 and of the foot portion 32 of the shell portion 30. On its other end 95d, the angle adapter 95 carries two rotatable locking hooks 99 constructed in the form of eccentrics, which likewise engage into pertinent perforations 99' in the wall areas of the leg portion 31 and of the foot portion 32 of the shell portion 30; in this case, the locking is effected by the rotation of the looking hooks 99 inserted into said perforations 99' so that a press fit free from play, more particularly on the oblique areas of the bead-like marginal reinforcements 93, is achieved (FIG. 10). The number of the stationary locking hooks 98 and the rotatable locking hooks 99 can be arbitrarily chosen. However, it is essential that in each case a stationary locking hook 98 and a rotatable locking hook 99 corresponds to each other and engages into the perforations 98' in the leg portion 31 and into the perforations 99' in the foot portion 32 of the shell portion 30.

It is possible, however, to employ differently constructed fastening means in lieu of the locking hooks 98, 99.

By preference, the plate-shaped angle adapter 95 is comprised of a springably elastic material, expediently a plastic.

The two shell portions 20, 30, are also comprised of plastic.

According to an embodiment, the preferred shell portions 20 or 30, comprised of plastic, possess wall areas constructed of solid walls. According to another embodiment, the wall areas of each shell portion 20 or 30 are constructed so as to be latticed while perforations are formed between the intersecting lattice bars, which may also be constructed in the form of strips or bands. This construction has the advantage that a sleeve-like padding disposed between the wall of the shell-like member and the extremity is positionally secured and disposed so as to be slip-proof, in as far as the readily deformable padding walls are pressed into the perforations of the shell-like member wall lattice in such a way that padding sections issue in a bead-like fashion from the perforations or come to rest in the same and thus are retained in their position by means of the lattice bars delimiting the perforations.

A further possibility of the angular adjustability of the foot portion 32 relative to the leg portion 31 of the anterior shell portion 30 consists, according to FIG. 5, in that the foot portion 32, which is adjustable in relation to the leg portion is connected with the aid of an accordion or concertina bellows-like constructed section 91 proceeding transversally to the longitudinal direction of the leg portion. Section 91 is provided with a plurality of folded and film hinge-like interconnected materials strips 91a, in which case the swivel hinges 35 which interconnect the foot portion 32 and the leg portion 31 and are constructed laterally to the shell-like member 10, are provided with angle locking means. In this embodiment, the area 91 corresponding to the window-like perforation 92, which is otherwise closed by means of the plate-shaped angle adaptor 95 between the foot portion 32 and the leg portion 31, is filled by means of a portion 91 that consists of the same material from which the shell portion 30 is also fabricated. This portion 91 is constructed along the lines of the bellow of an accordion or concertina, the individual strips of material 91 a being interconnected in a film-hinge-like mode so that in dependence of the respective angular position of the foot portion 32 relative to the leg portion 31 of the shell portion 30, this elongatable portion 91 adapts itself. The angle locking means, provided within the area of the swivel hinges 35, are contoured in a manner known per se; they comprise fixation means, such as setscrews, so that the predetermined angular position can be retained and changed only after the angle locking means has been disengaged.

In FIGS. 3 to 10, the shell portions are illustrated in the form of solid sectional portions for the sake of clarity. However, this schematic depiction must not be allowed to hide the fact that all shell portions possess the latticed or ribbed structure as shown in FIGS. 1 and 2.

Figure 11:
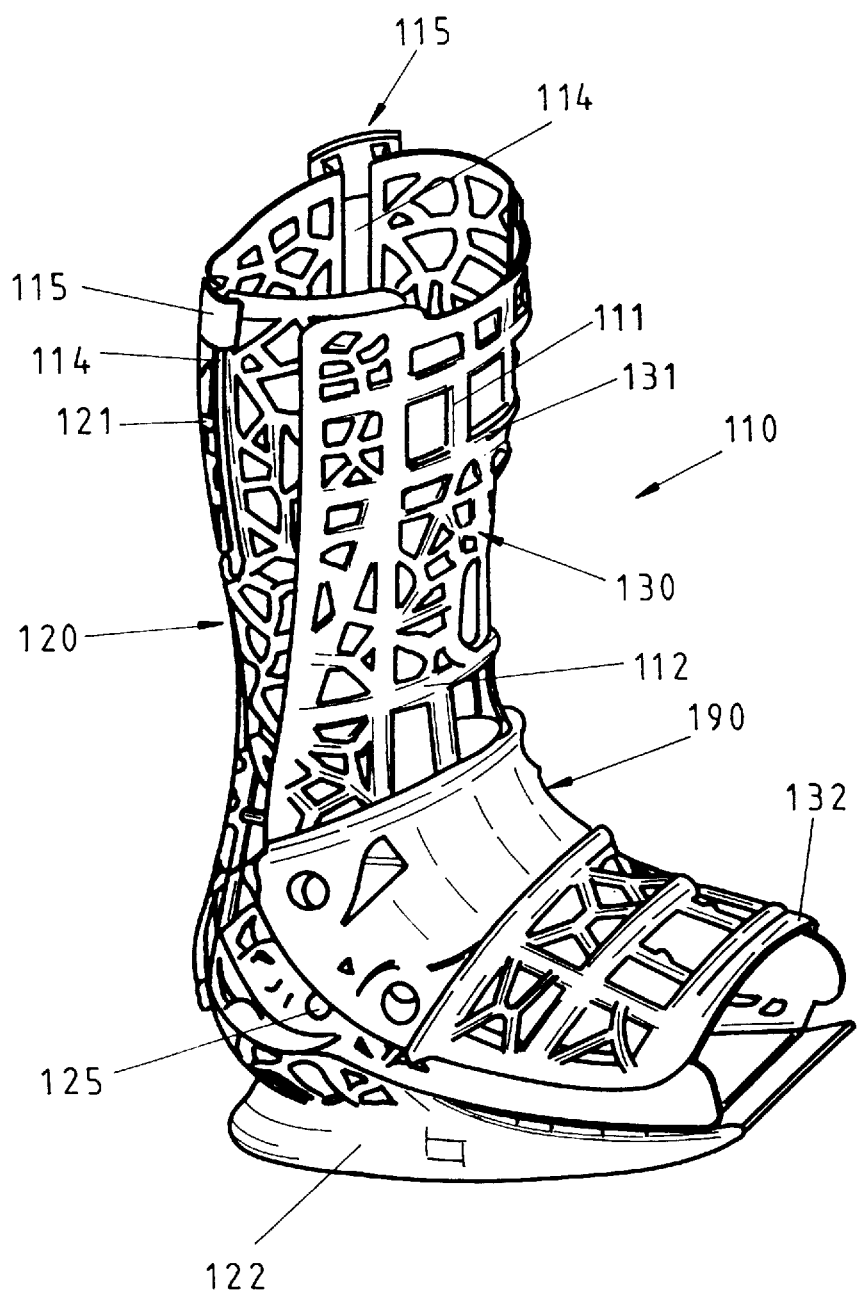
FIGS. 11 & 12 each show different embodiments of the device in a perspective view.
Figure 12:
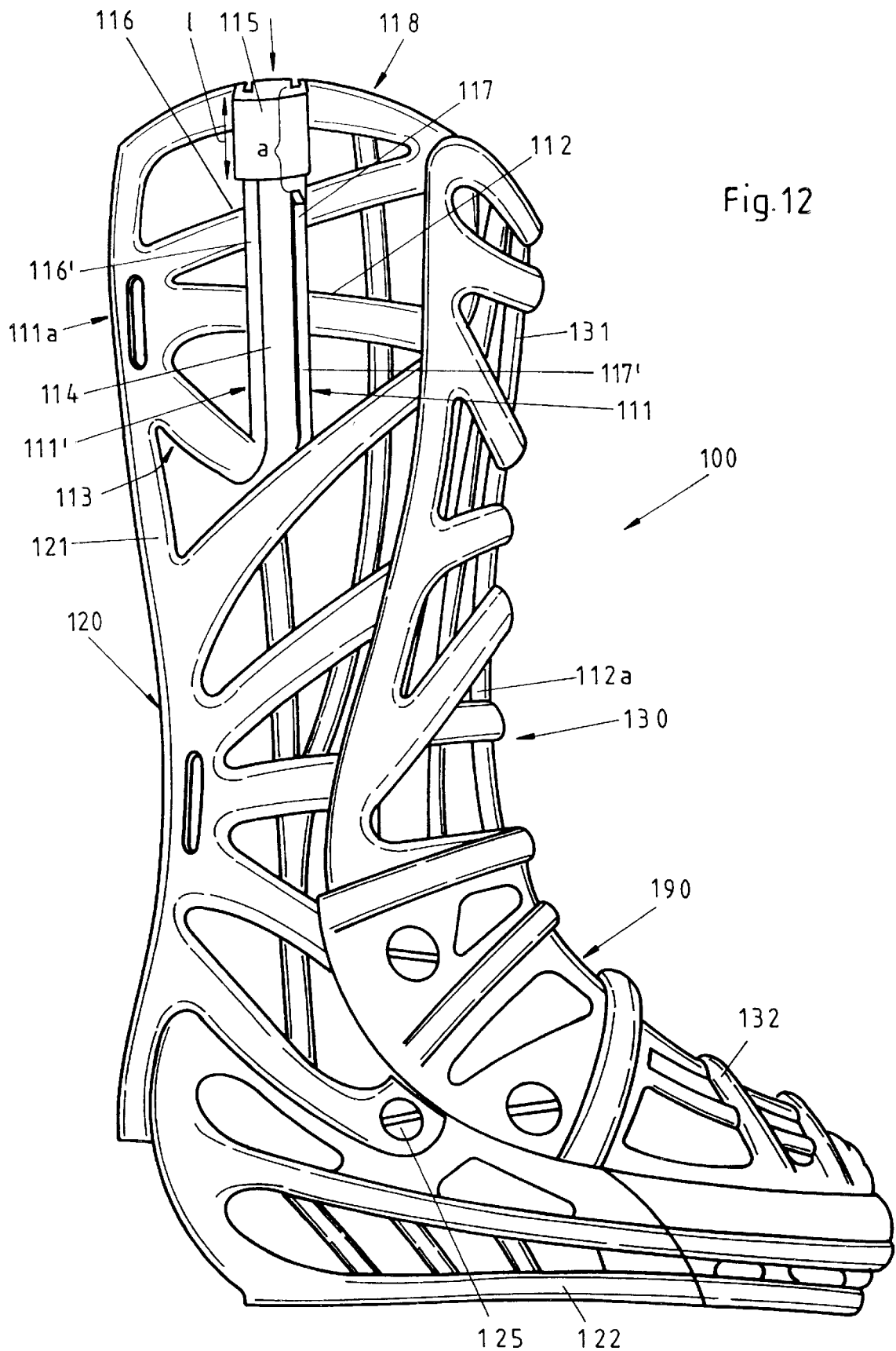

The device illustrated in FIGS. 11 and 12 for the ensheathing fixation of extremities is constructed, in its fundamental conception, in accordance with the embodiment described in the foregoing and depicted in FIGS. 1 and 2. Coinciding component parts are identified with the same reference number with a preceding "1".

In the upper leg portion 121, two longitudinal pairs of ribs, disposed in a side-by-side arrangement, are each provided with a gap 114 that is bridged with the aid of a connecting means 115. At least one gap 114 is variable in its width so that the leg portion can be adapted to the calf of the patient.

Figure 13:
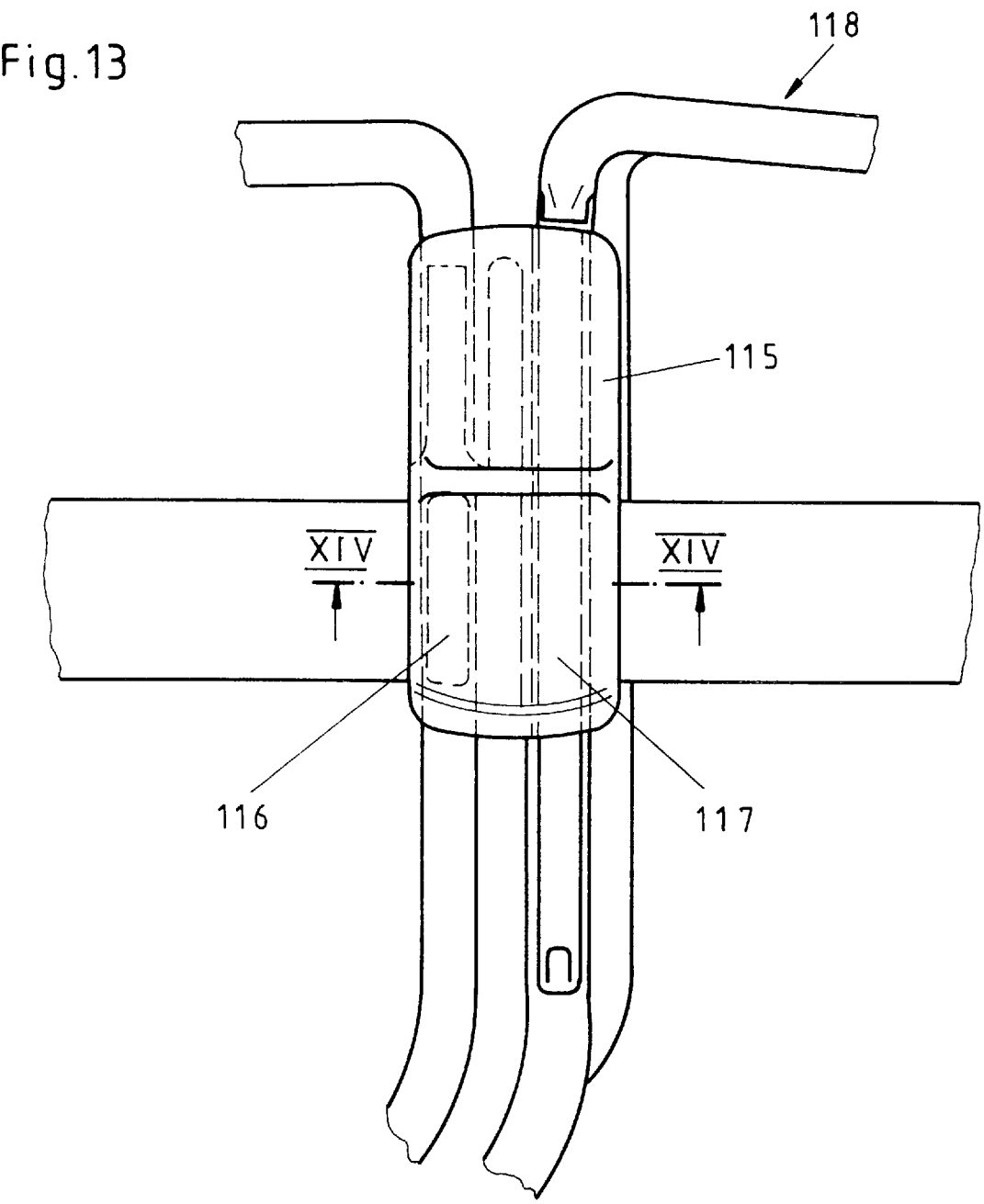
FIG. 13 shows an enlarged partial view of the leg portion to part construction with an adjustment possibility provided by a sliding member.
Figure 14:
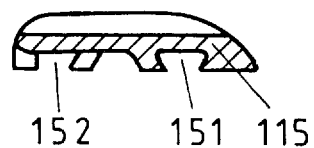
FIG. 14 shows a section along the Line XIV—XIV as per FIG. 13.
Figure 15:
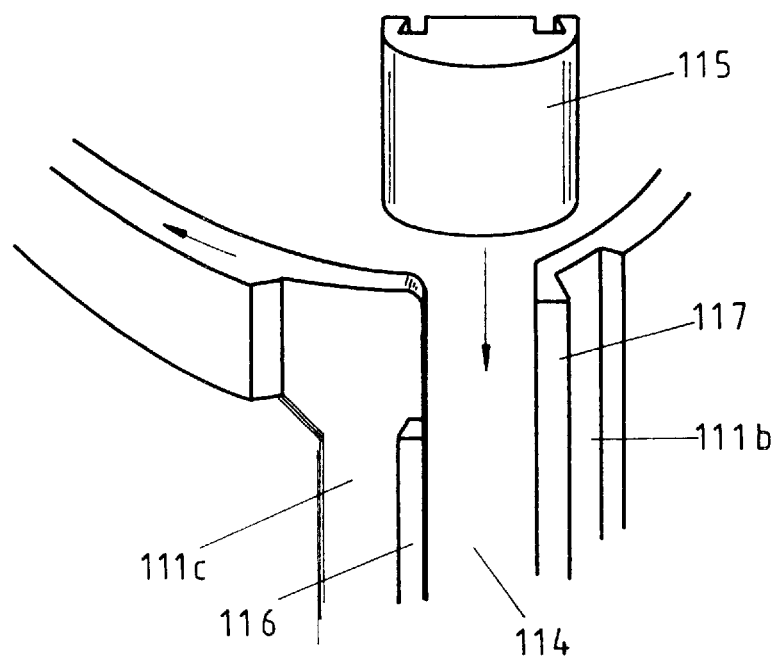
FIG. 15 shows a further embodiment of a sliding member.
Figure 16:
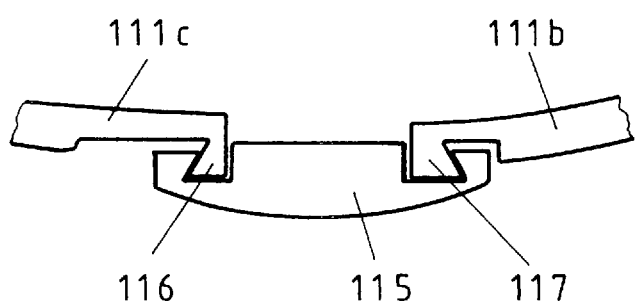
FIG. 16 shows a view from the top of the construction as per FIG. 15.
Figure 22:
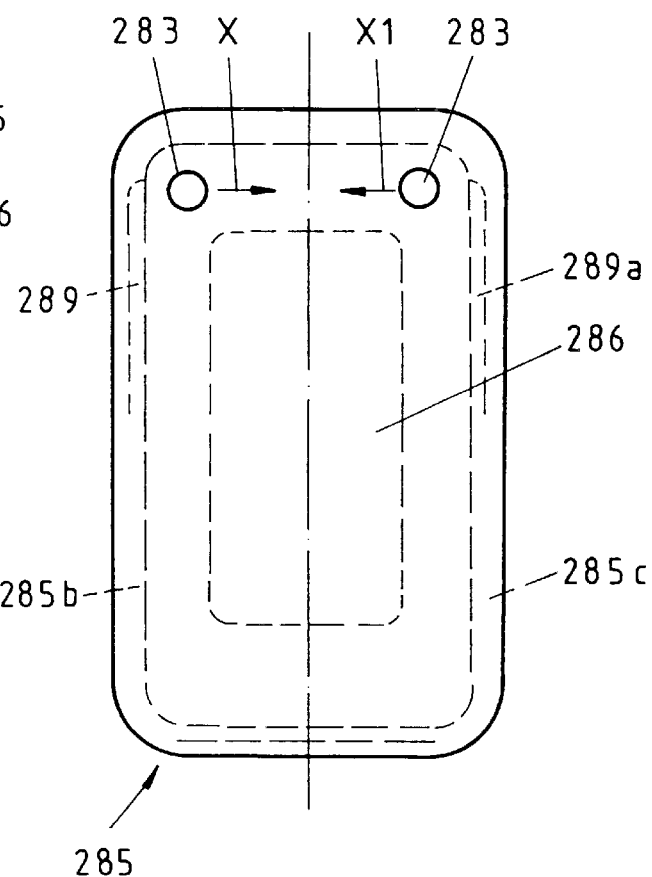
FIG. 22 shows in a front view the plate-shaped angle adapter.

In the embodiment that is shown in greater detail in FIGS. 12 and 13, two bead-like, rib-like raised points 116 and 117 on spaced-apart longitudinal ribs 111 serve as guide ways for the sliding member 115. The bead-like raised point is, on this occasion, constructed up to the top rim 118 of the upper part of the leg portion, while the raised point 117 terminates at a distance which is greater than the length 11 of the sliding member 115. It is possible that the sliding member 115, in the position shown in FIG. 22, is attached to the shell portion 120, while still being detached from the shell portion 130. As can be gathered from FIG. 13, beads are fitted on two spaced-apart longitudinal ribs 111, 111' in the form of guide rails 116' and 117', over which the sliding member 115 (shown in section in FIG. 13) engages. This fitting is such that the grooves 151 and 152 there exhibit a dovetail-type contour which is adapted to the bead-like raised points 116 and 117 as far as the configuration is concerned. In a case different from the embodiment depicted in FIG. 12, the guide rail 117' is constructed so as to be extended in the downward direction, whereas the rail 16 has only one length that corresponds to a partial length of the sliding member. The illustration in FIG. 15 corresponds to a perspective view of the embodiment in FIG. 12. FIG. 16 shows the closing means for fixating the oppositely located longitudinal ribs 111b and 111c that engage over the bead-like raised points 116 and 117.

Figure 17:
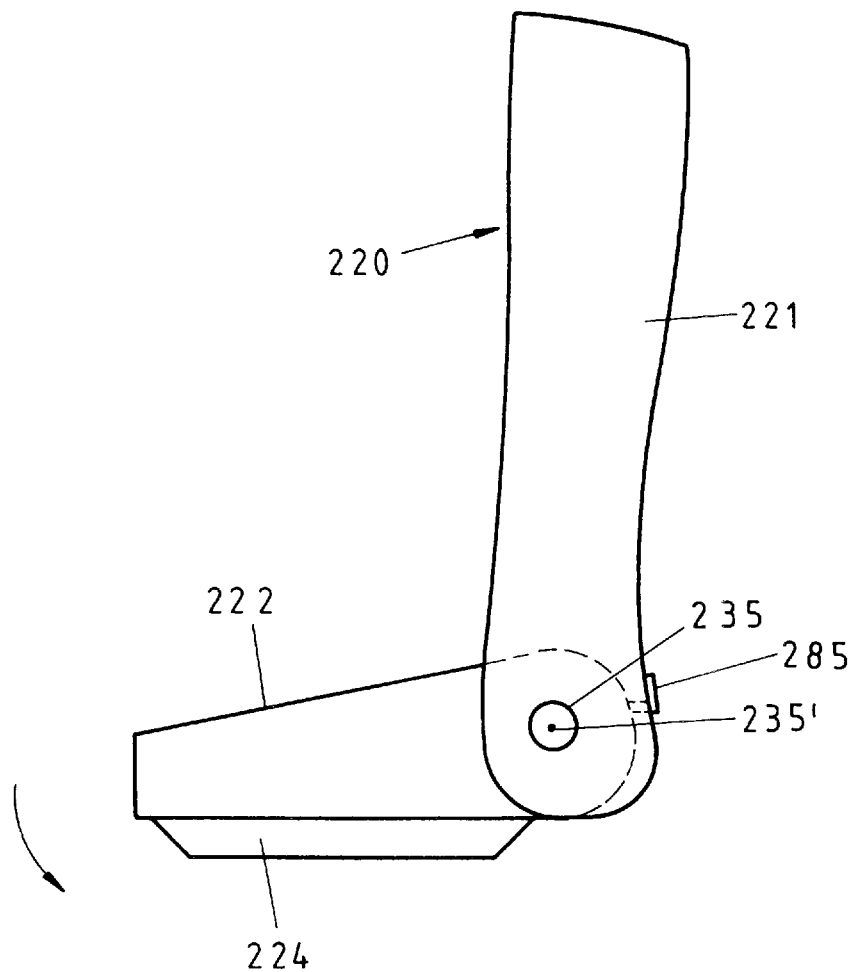
FIG. 17 shows a view of the posterior shell portion of the fixation device comprised of two L-shaped shell portions.

According to FIG. 17, the device for the ensheathing fixation of extremities comprises a posterior shell portion 220 possessing the configuration of an "L" and comprised of a leg portion 221 and a foot portion 222. The foot portion 222, with the aid of lateral swivel hinges 235, is swivellable about a swivel axis 235a so that the angle of the foot portion 222 relative to the leg portion 221 is adjustable. Expediently, this shell portion 220 is comprised of a plastic.

The foot portion 222 and the leg portion 221 of the posterior shell portion 220 are constructed so as to possess a shell-like configuration and so as to be open towards the top and towards the front so that an accommodation trough for the foot and the lower leg is provided. On the underside of the foot portion 222, an outsole 223 is provided, whose external configuration is adapted to the rolling motion of the foot when walking. For this the outsole 223 is constructed in the form of a walking rocker or is provided with a walking support.

Prior to the insertion of the extremity into the posterior shell portion 220, between the same and the shell portion, a deformable, vacuum-tight-constructed pad is provided with at least one valve (not depicted in the drawing) and comprised of a bladder, is inserted, in which a great number of mutually movable filling material particles are provided. The pad, which can be applied tightly so as to be well fitting to the limb section being treated, when, following an effected evacuation which can be expeditiously performed and taking up only relatively little time, becomes hard and inherently stable in the configuration created during the application procedure. As a result, in conjunction with the hard shell portion 220, a very sturdy sleeve which is well modeled onto the limb in question is produced that does not cause any pressure sores in the skin area since, when this structure is consolidated, it is not possible for a radial, inwardly directed pressure to be generated and, on the inside, no edges or projections can be formed either. Such an extremity ensheathed by a sleeve-like padding and positionally secured, is, subsequent to the insertion into the shell portion 220, retained and positionally secured with the aid of belt straps or similar devices (not depicted in the drawing). In lieu of a sleeve-like padding, it is also possible to provide a pad, a sock or suchlike pulled over the extremity in the interspace.

However, if a fixation that ensheathes the extremity were to be desired or become necessary, the posterior shell portion 220 could be combined with an anterior shell portion 230 so as to constitute a shell-like member 210, in which case the anterior shell portion 230 also possesses an L-like configuration with a leg portion 231 and a foot portion 232. The foot portion 232 can be disposed stationarily in relation to the leg portion 232 of the anterior shell portion 230 and in a predetermined angular position, such as 90°. Such an anterior shell portion 230 is always employed when the extremity in the posterior shell portion 220 is arranged in an angular position of 90° of the foot relative to the lower leg of the patient. The possibility also exists of inserting an anterior shell portion 230, in which the foot portion 232 relative to the leg portion 231, can be disposed in various angular positions, and where the foot portion 232 is then lockable in the predetermined angular position.

The anterior shell portion 230, too, is constructed in a shell-like configuration in the direction towards the foot and the lower leg, in which case both shell portions 220, 230 are then constructed in a way that the anterior shell portion 230 is insertable into the posterior shell portion 220 in such a way that the lateral wall sections of the shell portion 220 engage the lateral wall sections of the shell portion 230 in a section-wise fashion.

Both the shell portion 220, as well as the shell portion 230, possess an approximately semicircular cross-section so that, when the shell portions are inserted into each other, a section-wise engagement over the side wall sections of the two shell portions 220, 230 takes place. In order to laterally engage around the lower leg and also the foot, the shell portions 220, 230 possess a certain degree of elasticity, in which case the elasticity of the side walls of the two shell portions 220, 230 expediently increases from the central areas of the shell portions towards the free margins of each leg portion.

The closing elements are expediently provided on the longitudinal marginal areas of the foot portion and the leg portion of the posterior shell portion 220 and/or of the anterior leg portion 230. These elements are, more particularly, comprised of Velcro strip fasteners, and provide in a very simple and expeditious manner the slight contact pressure of the padding on the closed shell-like member that is necessary prior to the evacuation being performed. In this way it is possible to produce a sleeve of absolutely correct fit and to fixate the same by means of the Velcro strip fasteners. Once the evacuation has been effected, a sleeve is available which, consolidated in itself, is stabilized in its configuration and which retains the extremity in a positionally secured manner.

Figure 18:
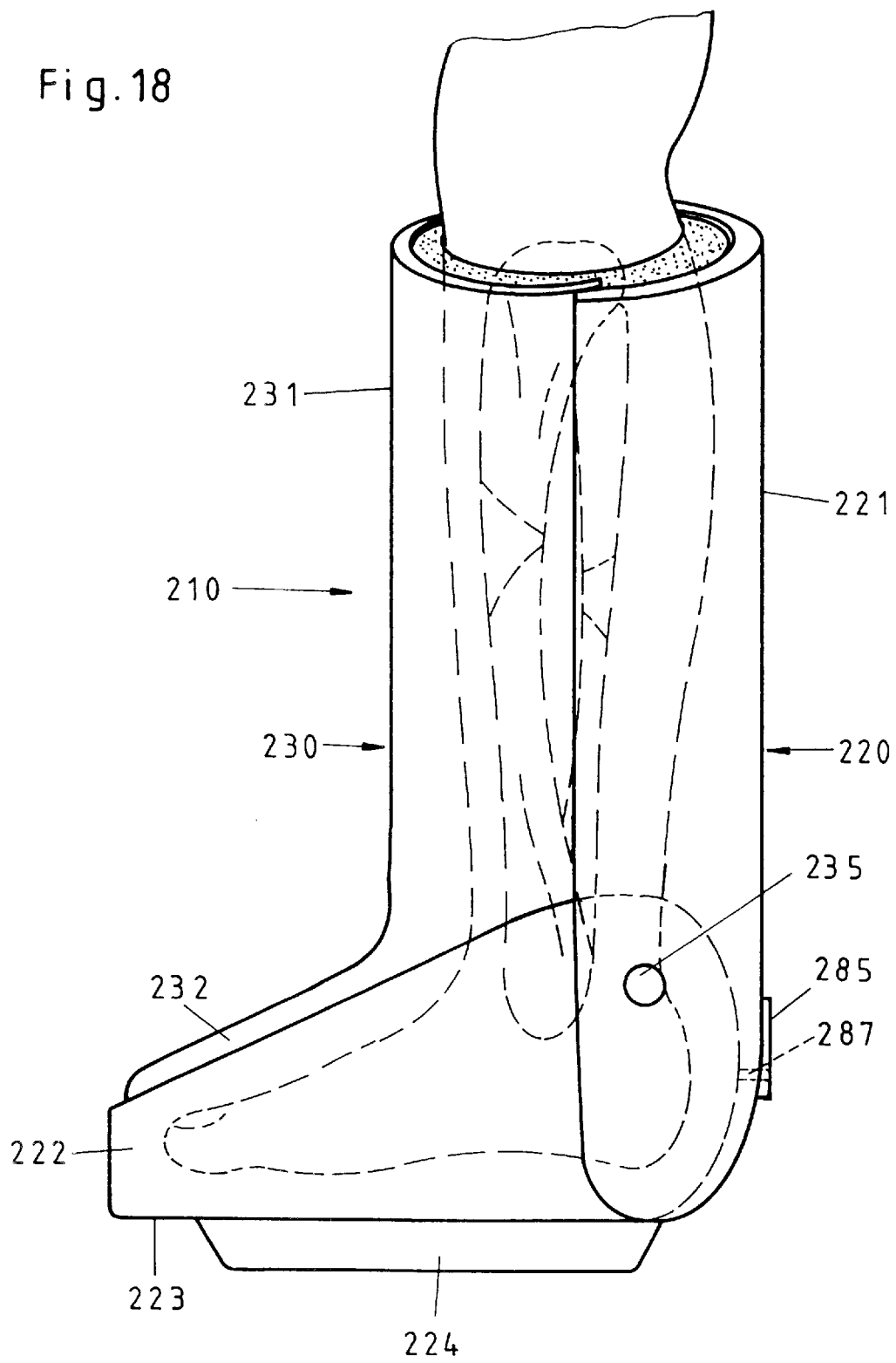
FIG. 18 shows a side view of the fixation device comprising a shell-like member with two L-shaped shell portions.
Figure 19:
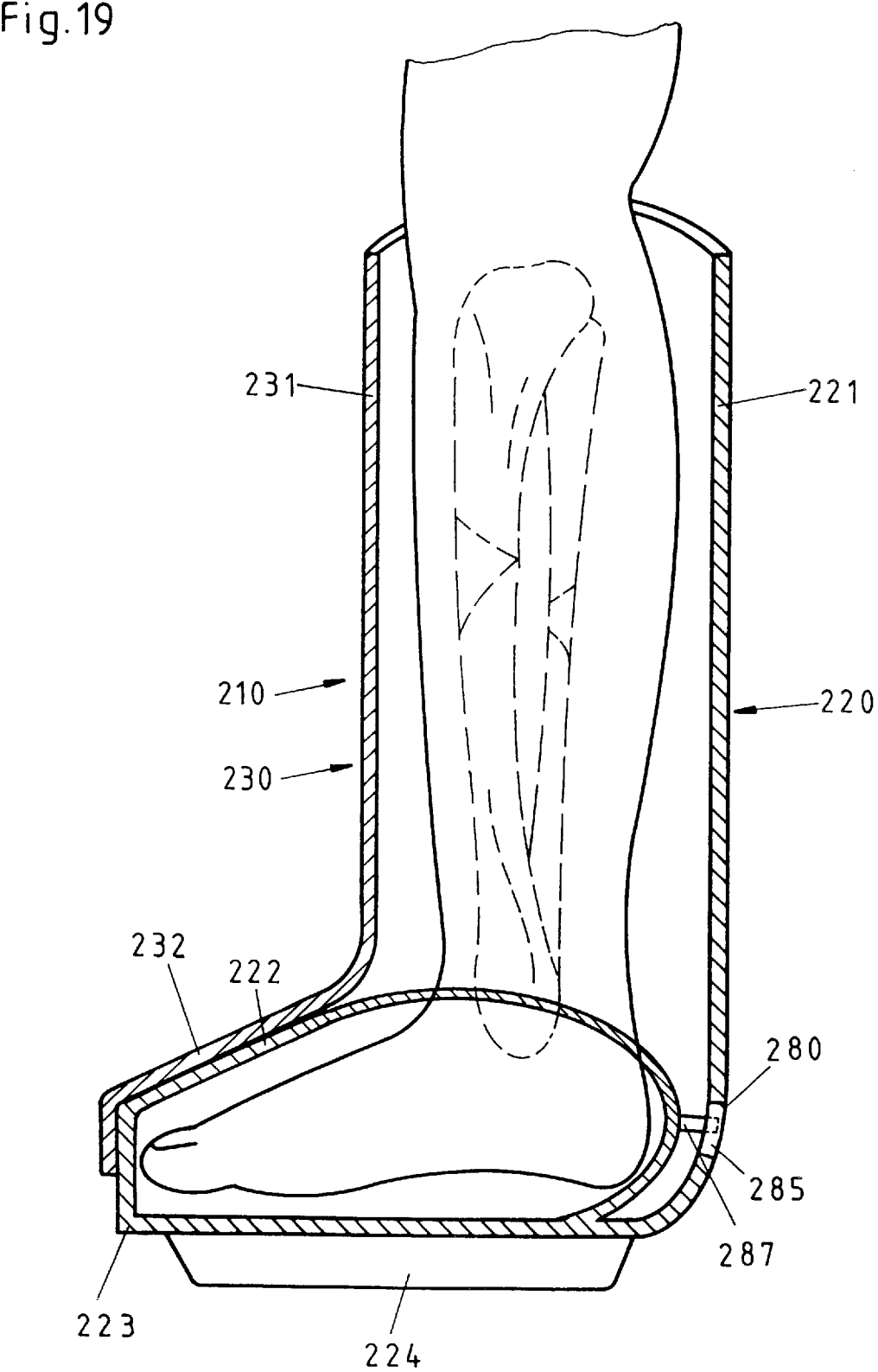
FIG. 19 shows the fixation device partly in a side view and partly in a vertical longitudinal section.
Figure 20:
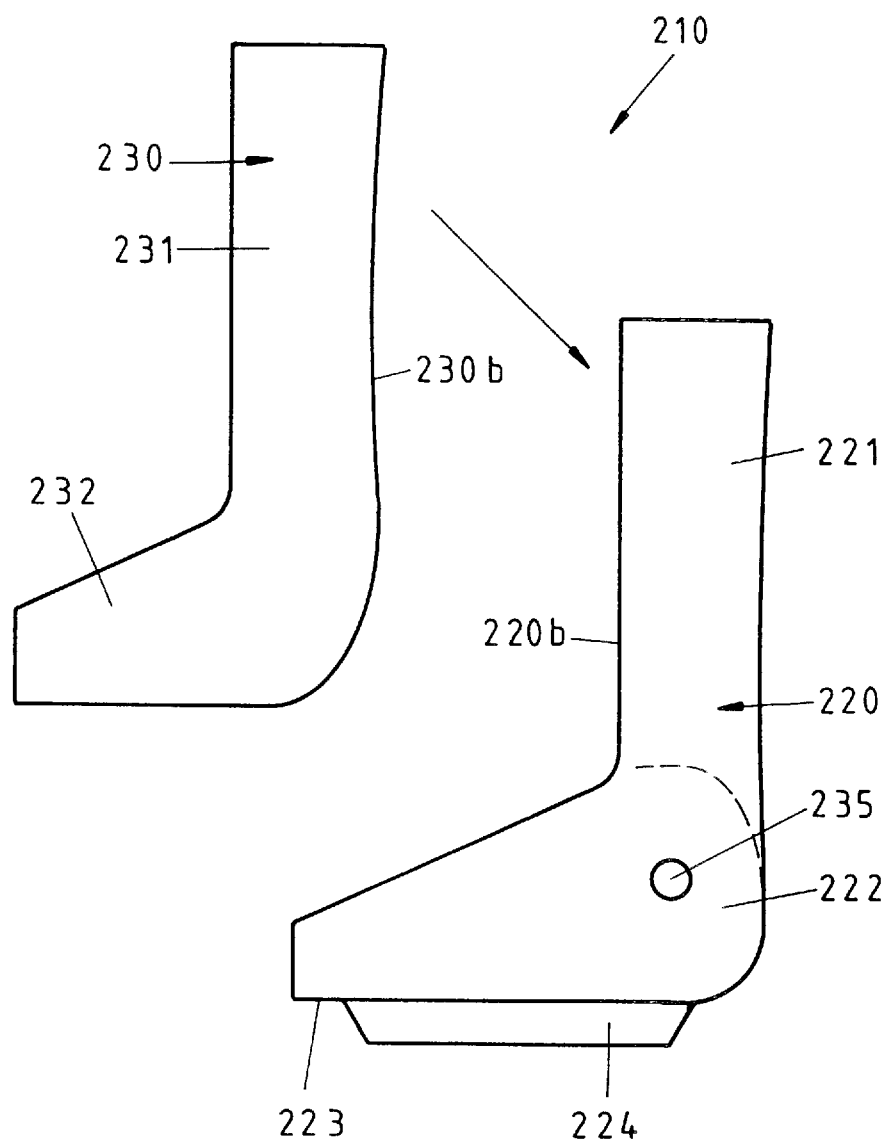
FIG. 20 shows in a side view the two L-shaped shell portions of the shell-like member prior to their being tightened.
Figure 21:
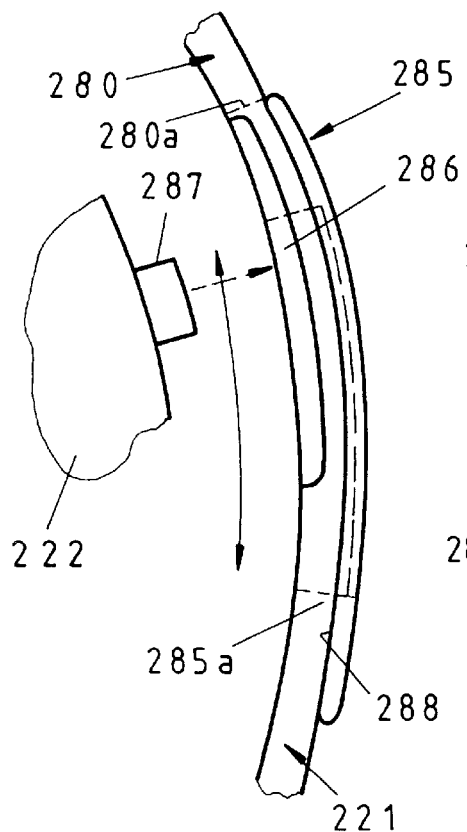
FIG. 21 shows in a side view the angle adjustment or setting means comprising a plate-shaped angle adapter and a pin engaging into the latter.

In order to be able to effect an optimal angular adjustment of the foot relative to the lower leg, or of the foot portion 222 relative to the leg portion 221 of the posterior shell portion 220, in the rearward wall area of the leg portion 221 of the shell portion 220, to be more precise, a window-like perforation 280 is constructed. Into perforation 280 a plate-shaped angle adapter 285 is inserted, which is provided with an engagement aperture 286, into which, for securing the angle between the foot portion 222 and the leg portion 221 of the posterior shell portion 220, a pin engages which is formed onto the foot portion 222 of the posterior shell portion 220 (FIGS. 18,19 and 21).

Figure 23:
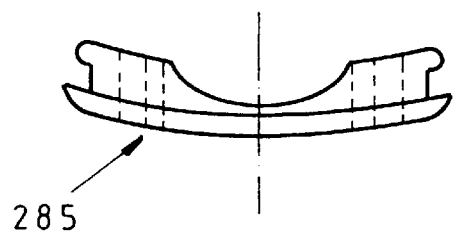
FIG. 23 shows a view from above of the angle adapter as per FIG. 22.

The angle adapters 285, which are insertable into this window-like perforation 280 in the rearward wall of the posterior shell portion 220, possess engagement apertures 286 for the pins 287 in different positional arrangements relative to the angle adapter surface. This enables the adapters to fixate the foot portion 222 relative to the leg portion 221 of the posterior shell portion 220 in predetermined and specific angular positions (FIGS. 22 and 23).

The window-like perforations 280 in the wall of the posterior shell portion 220 are constructed so as to be approximately rectangular. The angle adapter 285 possesses a construction corresponding to the configuration and dimensions of this window-like perforation 280 so as to, by way of example, be retained with the aid of clamping fit in the window-like perforation 280. The length of the engagement aperture 286 in the angle adapter 285, according to one embodiment, corresponds to an adjustable angular area of the foot portion 222 relative to the leg portion 221 of the shell portion 220.

The cross-sectional configuration of the pin 287 may be square, rectangular or circular or possess some other geometric form. The engagement aperture 286 possesses a configuration that corresponds to the cross-sectional shape of the pin 287.

Figure 24:
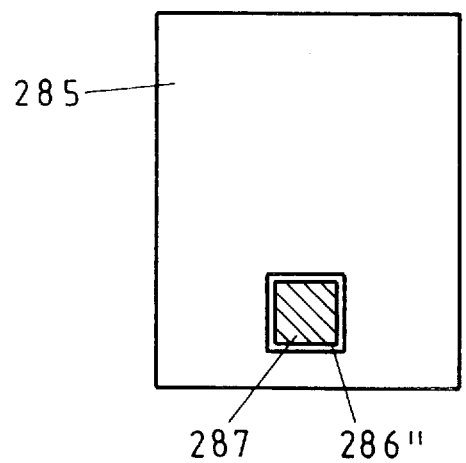
FIG. 24 shows a schematic view of an angle adapter for the adjustment or setting of an angle corresponding to the normal angular position of 90°.

In order to have angle adapters 285 available for the most widely varying angular ranges of the foot portion 222 relative to the leg portion 221 of the shell portion 220, according to another embodiment, the engagement aperture 286" for the pin 287 is constructed in the lower area of the angle adapter 285 (FIG. 24). In this embodiment, an angular position of the foot portion 222 relative to the leg portion 221 is obtained in an angle of 90°, which corresponds to the normal angular position between the foot and the lower leg.

Figure 25:
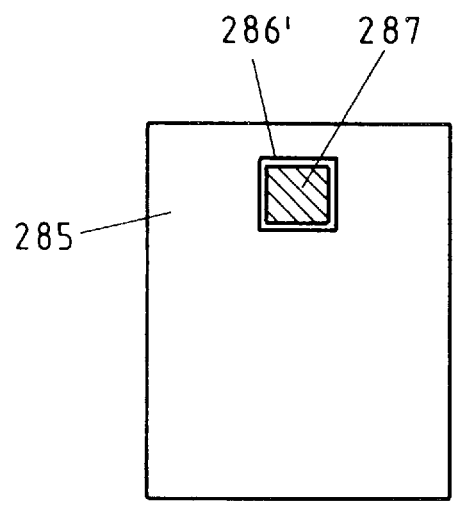
FIG. 25 shows a schematic view of an angle adapter for adjusting or setting an angle corresponding to the pes equinus position of 120°.

If it is intended to obtain a pes equinus position of 120° as the angle between the foot portion 222 and the leg portion 221, then an angle adapter 285 is employed in which the engagement aperture 286' for the pins 287 is constructed within the upper area of the angle adapter 285 (FIG. 25).

Figure 26:
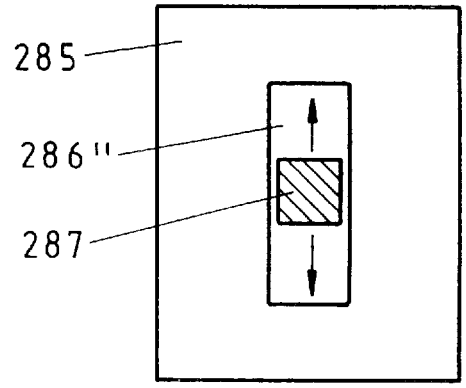
FIG. 26 shows a schematic view of an angle adapter having an angle adjustment or setting possibility covering a greater range.

In order to be variable in a larger angular range, the angle adapter 285 may also possess an expediently slot-shaped engagement aperture 286''' for the pin 287, in which case, it is advantageous when the pin 287 is constructed in the form of a setscrew (see FIG. 26).

If, for instance, three angle adapters 285 possessing different dispositions of the engagement apertures 286', 286" and 286''' are made available, then, with these three angle adapters 285, the entire range of angular positions is available and adjustable. In this case, the angle adapter 85 with the engagement apertures 286' and 286" can also be employed as a sole structural element, in which connection it is possible for the angle adapter 85 with the engagement apertures 286' and 286" to be employed as a sole structural element. Here the angle adapter 285 possesses, either within the upper area or within its lower area, an engagement aperture 286' or 286", whereby the possibility exists, by means of a differing insertion of this angle adapter into the window-like perforation 280, to optionally determine both angle ranges, viz. firstly the range having the angle of 90° and the angle of 120°. This is done so that solely the angle adapter 285 illustrated in FIG. 24, rotated through 180°, is then inserted into the window-like perforation 280 in the leg portion 221 of the posterior shell portion 220 so as to obtain the engagement aperture 286' within the upper area so that, when the pin 287 engages into the engagement aperture 286' assuming this position, the splayfoot position is reached and obtained so that, already with a single angle adapter, the angular positions of 90° and 120° are achievable. However, on this occasion, the disposition and allocation of the engagement aperture in the angle adapter 285 in relation to the entire area of the angle adapter is such that, when the angle adapter 85 is inserted following a performed rotation through 180°,the angle necessary for the pes equinus position is achieved.

The plate-shaped angle adapter 285 is, by way of example, retained by clamping fit in the window-like perforation 280 in the leg portion of the posterior shell portion 220. According to FIGS. 21 to 23, the plate-shaped angle adapter 285, on its circumferential rim 285a, is provided with a circumferential groove or grooves 288 extending over oppositely located areas for engagement into the rim 280a delimiting the window-like perforation 280. By preference, the plate-shaped angle adapter 285 is comprised of a springably elastic material, expediently a plastic and is, in this case, retained by means of clamping fit on the circumferential rim 80a of the window-like perforation 280. By virtue of the springably elastic construction of the marginal sections, the plate-shaped angle adapter 285 is merely pressed into the window-like perforation 280 in such a way that the angle adapter 285 is retained within the marginal area of the window-like perforation 280. The circumferential rim of the angle adapter 285 and the rim delimiting the window-like perforation 280 is provided with engagement contours, a marginal contouring or profiling that can be effected in the manner of the groove and spring construction.

According to another embodiment, as shown in FIG. 22, the plate-shaped angle adapter 285, on its two longitudinal side edges 285b, 285c, possesses uniformly upwardly expanding reinforcements 289, 289a comprised of a springably elastic material so that the clamping fit is additionally increased within the marginal area of the window-like perforation 280. These reinforcements 289, 289a which expand uniformly in the upward direction on the lateral rims of the plate-shaped angle adapter 285 may also be constructed in the form of movable strips that are connected to a mechanism in such a way that, when the mechanism is actuated, these uniform reinforcements 289, 289a are swung into the rim of the angle adapter 285. As a result, when the angle adapter 285 is not retained in the window-like perforation 280, the angle adapter 285 can then, subsequent to the so-called unlocking of the angle adapter 285, be removed from the window-like perforation 280. Also otherwise constructed locking means for arresting and mounting the angle adapter 285 in the window-like perforation 280 can be provided.

The replacement of the angle adapter 285 can be effected with the aid of pliers-like opening tools not depicted in the drawings. For this, the plate-shaped angle adapter 285, within its upper area, is provided with two spaced-apart perforations 283, into which a pliers-like opening tool is insertable. As a result, in the case of divergent directions of movement in the direction of the arrows X, X1, the angle adapter 285 that is located within the engagement area of the tool is compressed and the release of the strip-like reinforcements 289, 289a from the marginal area of the window-like perforation 280 takes place. It is a precondition that a pertinent springably elastic construction of the angle adapter 285 exists, in which case, however, the angle adapter 285 has to possess a high degree of inherent rigidity within the area of the engagement aperture 86 for the pin 287.

The shell portions 220 and 230 which are preferably comprised of plastic, possess wall areas of solid wall construction, according to an embodiment. According to a further embodiment, the wall areas of each shell portion 220 or 230 are of latticed construction with the formation of perforations between the intersecting lattice bars which can also possess a strip-like or band-like configuration. This construction produces the advantage that a sleeve-like padding between the wall of the shell-like member and the extremity is disposed so as to be positionally secured and slip-proof in so far as the easily deformable padding walls are pressed into the perforations of the wall lattice of the shell-like member in such a way that sections of the padding issue in a bead-like fashion from the perforations are retained in their position by the lattice bars which delimit the perforations.

The engagement apertures 286, 286', 286", 286''' in the angle adapter 85 for the pin 287 do not have to be constructed in the form of a perforation. It is also possible for groove-like depressions or recesses to effect the positional securing and the fixation of the pin 287 in the angle adapter 285.

Moreover, the possibility exists of disposing the pin 287 on the inner wall area of the rear wall of the posterior shell portion 220, which then engages into a pertinently constructed and aforedescribed angle adapter 285 that is disposed in the rearward area of the foot portion 222 of the shell portion 220.

Figure 28:
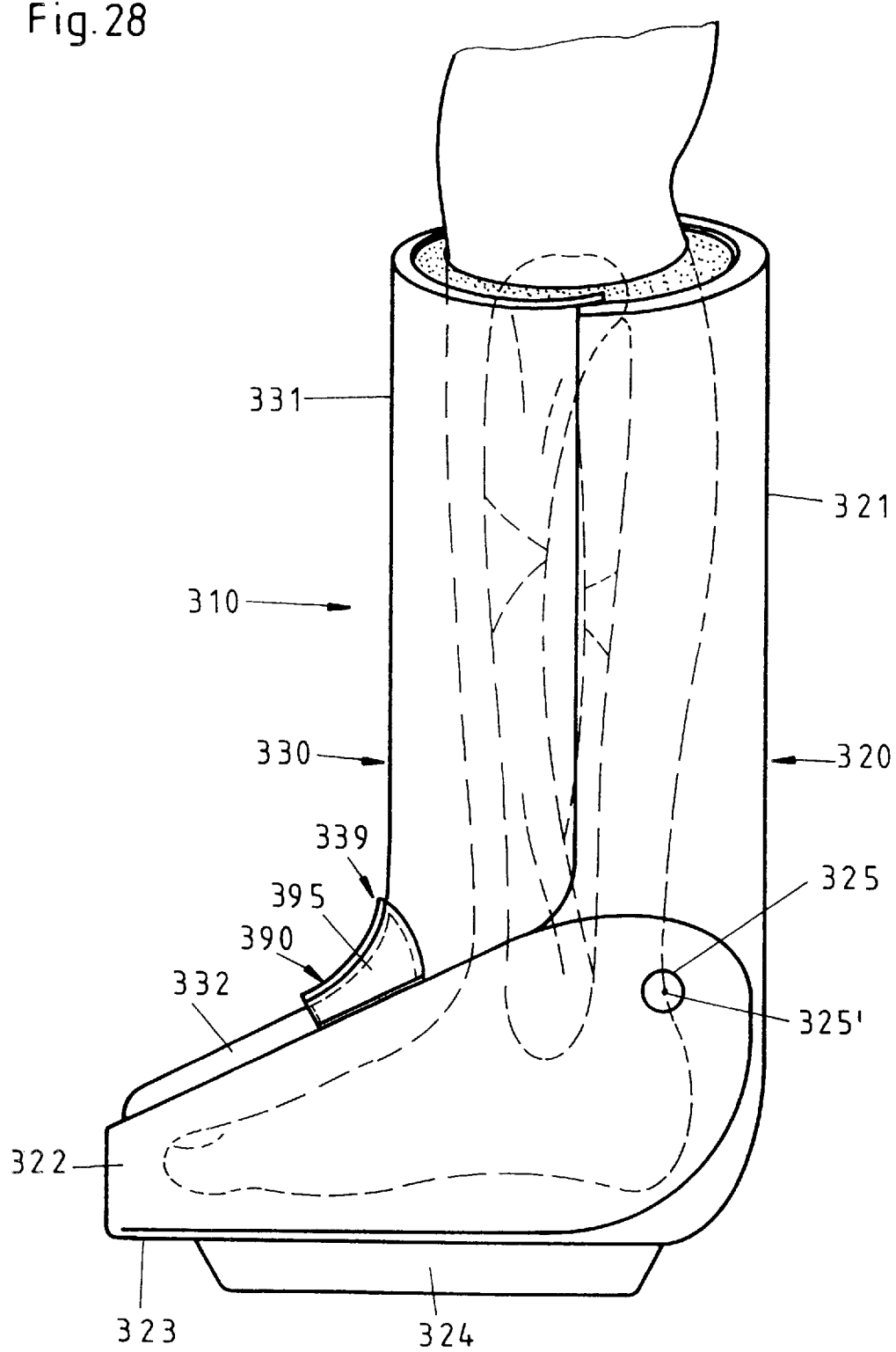
FIG. 28 shows a side view of the fixation device comprising a shell-like member with two L-shaped shell portions.
Figure 29:
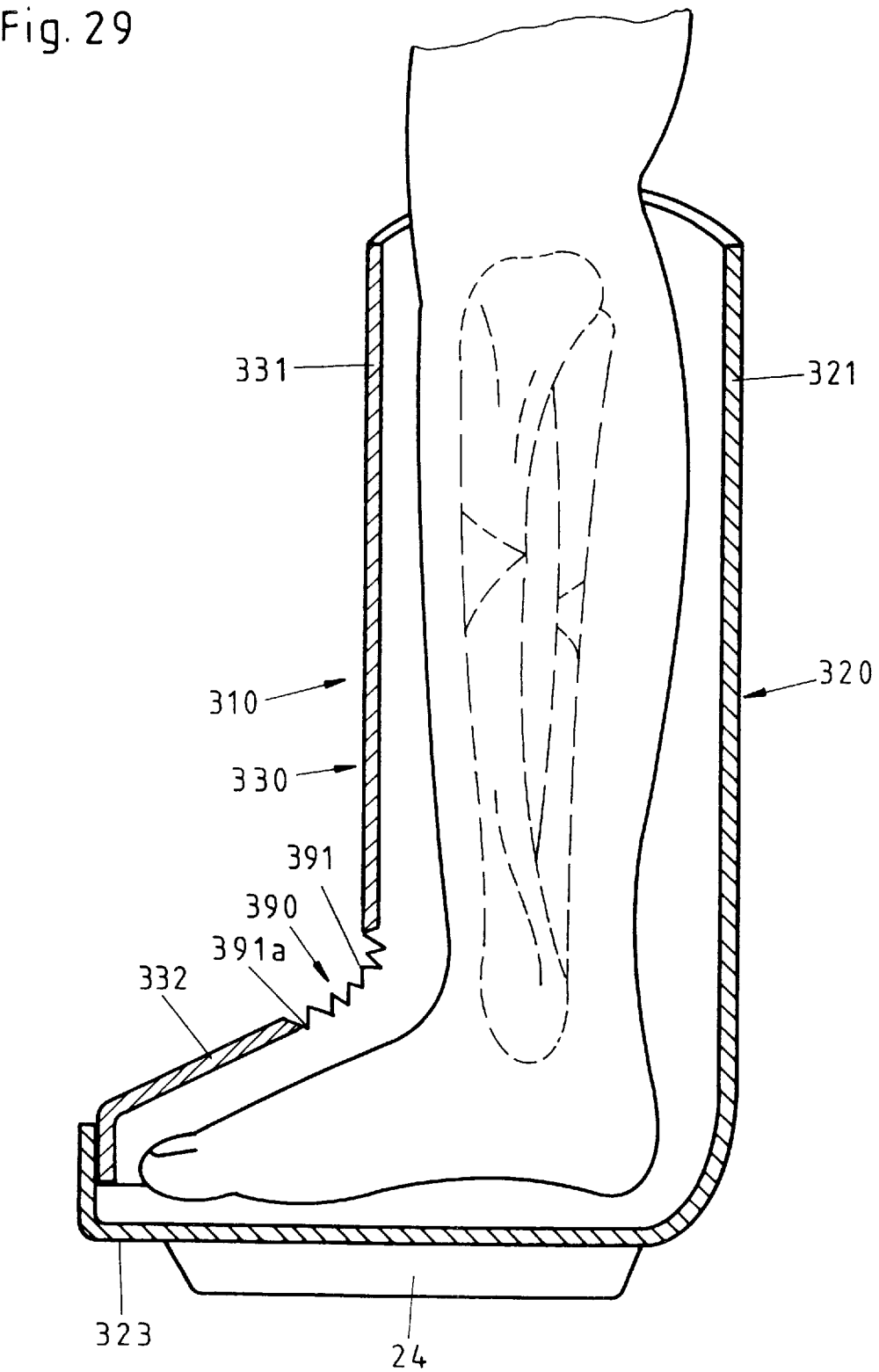
FIG. 29 shows the fixation device as per FIG. 28, partly in a side view and partly in a vertical longitudinal section.
Figure 30:
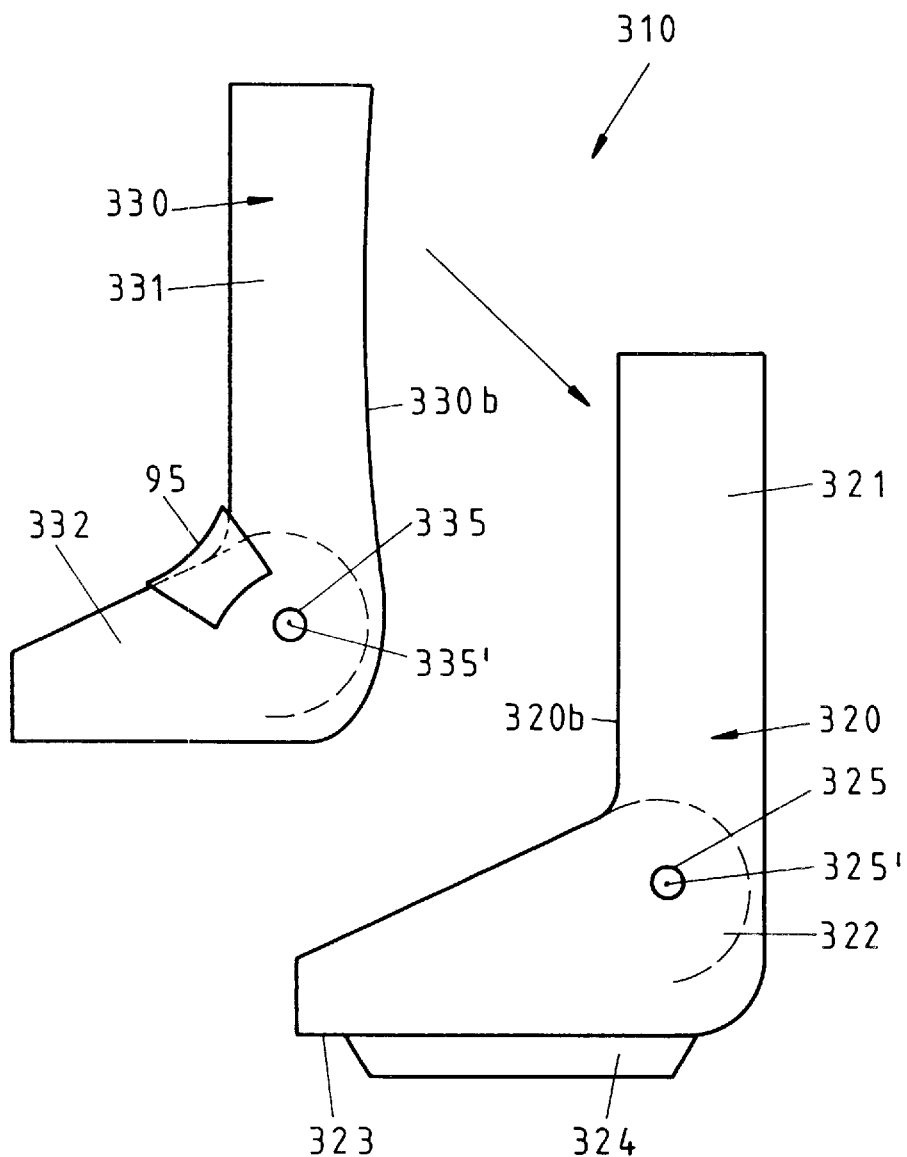
FIG. 30 shows in a side view the two L-shaped shell portions of the shell-like member prior to their being tightened.

The device for the ensheathing fixation of extremities, illustrated in FIGS. 28, 29 and 30, is in the form of a shell-like member 310 for the foot/lower leg region. The shell-like member 310 is comprised of two reciprocally tightenable shell portions, viz. a posterior shell portion 320 and an anterior shell portion 330, in which case both shell portions 220, 230 possess the approximate configuration of an "L". Each shell portion 320 or 330 is comprised of a leg portion 321 or 331 and a foot portion 322 or 332, in which case the foot portions 322, 332 are interconnected by means of lateral swivel hinges 325, 335 so that the foot portions 322, 332 are swivellable relative to the leg portions 321, 331 about swivel axes 325a, 335a. Both the shell portions 320, 330 as well as their swivel hinges 325, 335 are made of plastic.

The foot portions 322, 332 and the leg portions 321, 331 of the two shell-like members are constructed in a shell-resembling fashion so as to be open on one side so that, in the posterior shell portion 320, an accommodation trough for the foot and the lower leg is created. Also, the anterior shell-like member 330 is constructed in the same way so that it, with its leg portion 331 and its foot portion 332, can be attached to the leg portion 321 and the foot portion 322 of the posterior shell portion. On the underside of the foot portion 322 of the posterior shell portion 320, an outsole 323 is provided, whose external configuration is adapted to the rolling movement of the foot when walking. For this purpose the outsole 323 is constructed in the form of a walking rocker or provided with a walking support 324.

The foot portions 322, 332 and the leg portions 321, 331 of the two shell portions 320, 330 of the shell-like member 310 are, in the direction towards the foot and lower leg, constructed in the form of a shell. The design is such that the anterior shell portion 330 is insertable into the posterior shell portion 320 in such a way that the lateral wall sections of the posterior shell portion 320 engage section-wise over the lateral wall sections of the shell portion 330 (FIG. 29).

Both the shell portion 320 as well as the shell portion 330 possess an approximately semicircular cross-section so that, in the case of superposed shell portions, a section-wise engagement over the side wall sections of the two shell portions 320, 330 takes place. In order to be able to laterally engage around the lower leg and also the foot, the shell portions 320, 330 possess a certain elasticity. The elasticity of the side walls of the two shell portions 320, 330 expediently increases from their central areas of the leg portions to their anterior free margins of each shell portion.

The fastening means on the longitudinal marginal areas of the foot portion and the leg portion not shown in the drawing are comprised particularly of portions of Velcro strip fasteners. These fastening means provide in a very simple and expeditious fashion for the slight bearing pressure of the padding on the closed shell-like member which is necessary prior to the evacuation being performed. Thus, it is possible to produce a sleeve of absolutely perfect fit and to fixate the same with the aid of the Velcro strip fastener. After the effected evacuation, a sleeve is available which is consolidated in itself and stabilized in its configuration and which retains the extremity positionally secured.

It is possible to prevent a movement in the ankle of the patient because the angle of inclination of the leg portion relative to the foot portion is adjusted tightly about the swivel axis 325 or 335. A selection of this rigidly set or adjusted angle can be effected in dependence of the injury to be treated within the entire adjustable range of swivel angles. The fixation to a specific angle is accomplished by pertinently constructed adjustment means, in which case, in the posterior leg portion 320, a predetermination for the adjustment of an angle of 90° or 120° between the foot portion 322 and the leg portion 321 can be carried out by an angle adapter (not shown in the drawing).

In order to be able to effect an adaptation of the anterior shell portion 330 to the angular position of the foot portion 322 relative to the leg portion 321 of the posterior shell portion 320, the anterior shell portion 330 is provided with an angle adjustment means 390, by which the foot portion 332 can, in relation to the leg portion 331, be locked in a predetermined angular position. This angular position is coincident with the angular position of the foot portion 322 relative to the leg portion of the posterior shell portion 320.

Figure 27:
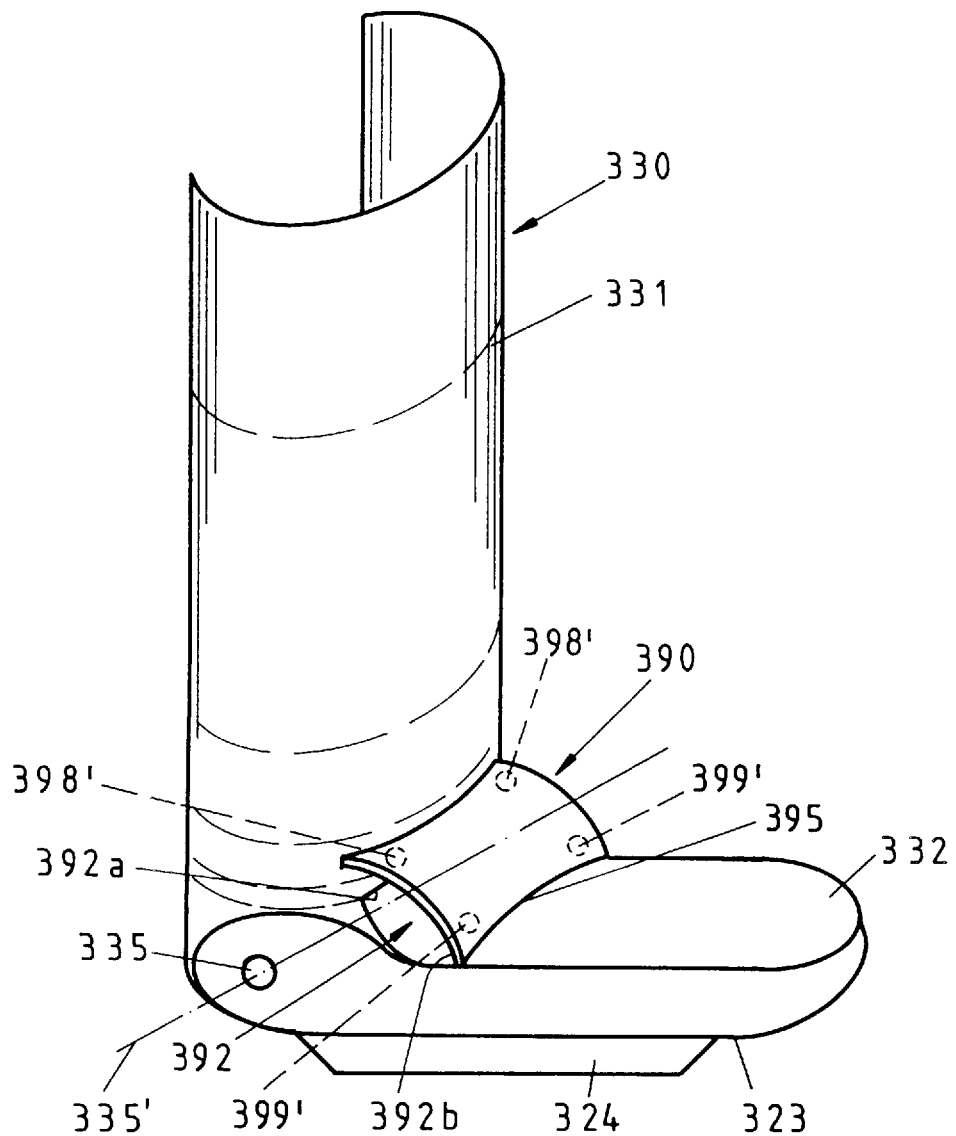
FIG. 27 shows a diagrammatical view of the anterior shell portion of the fixation device comprised of two L-shaped shell portions with inserted angle adapter.
Figure 31:
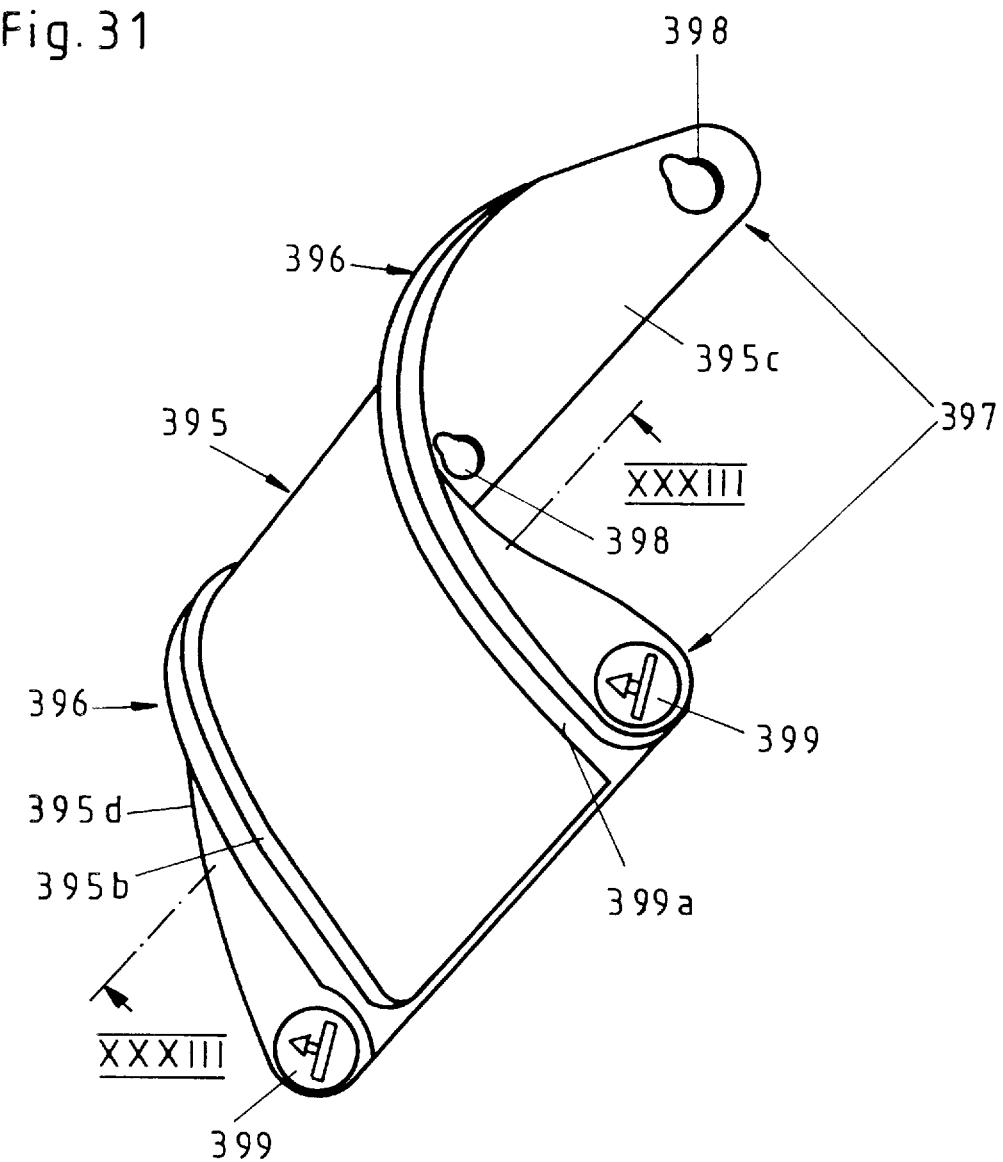
FIG. 31 shows in a diagrammatic view an angle adapter for an angular position of 90° between the foot portion and the leg portion of the anterior shell portion.

This angle adjustment means 390 is comprised of a plate-shaped adapter 395 that is disposed between the foot portion 332 and the leg portion 331 of the anterior shell portion 330, formed in correspondence with the external contours of the shell-like member 310 or the anterior shell portion 330. The angle adapter is detachably retained by means of click-stop and locking means 397 on the leg portion 331 and foot portion 332 of the anterior shell portion 330 (FIGS. 27 and 31). This angle adapter 395 engages in a lug-like fashion on the front side over the connecting area 339 between the foot portion 332 and the leg portion 331 of the anterior shell-like member 330.

Figure 32:
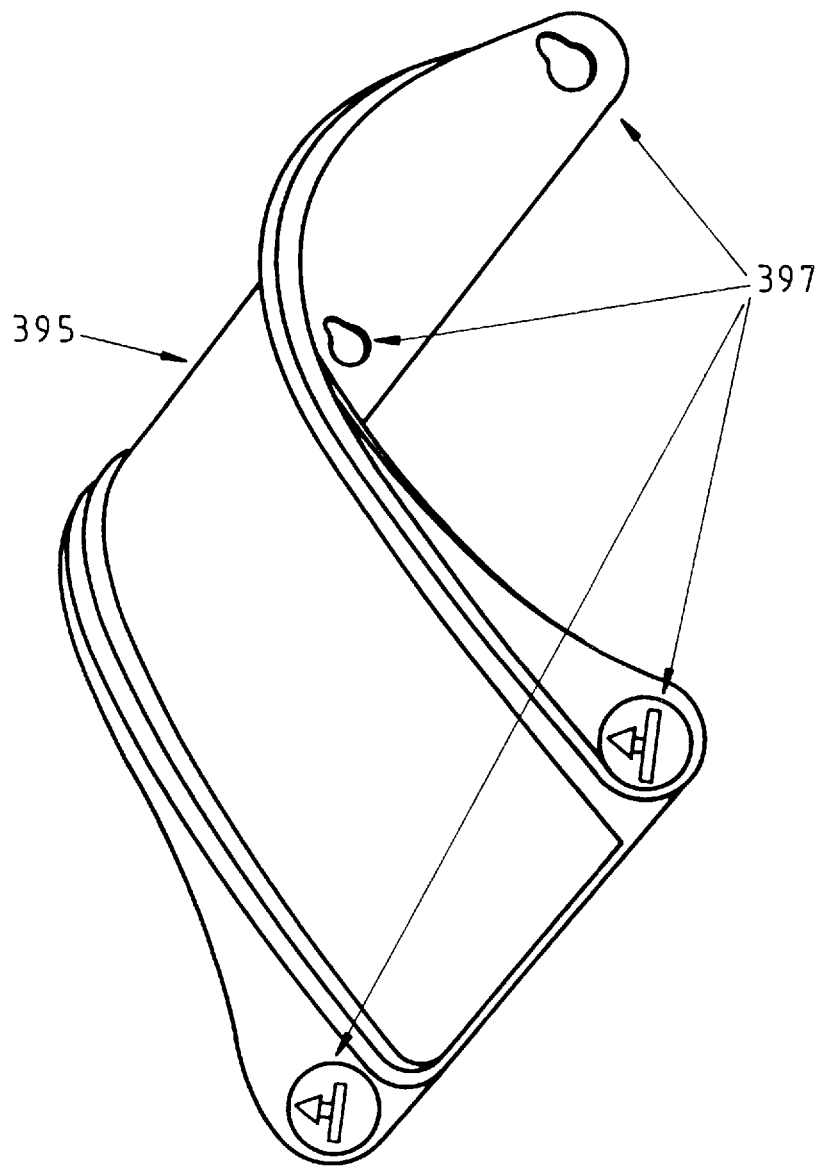
FIG. 32 shows in a diagrammatic view an angle adapter for an angular position of 120° between the foot portion and the leg portion of the anterior shell portion.

This plate-shaped angle adapter 395 possesses a width, by virtue of which the foot portion 332, relative to the leg portion 331 of the shell portion 330, assumes an angular position of 90° (FIG. 31). This angular position is the normal position between the foot and the lower leg. A further embodiment of the angle adapter 395 provides a width, by virtue of which the foot portion 332, relative to the leg portion 331 of the shell portion 330, assumes an angular position of 120° so that, when this embodiment of the angle adapter is inserted between the foot portion 332 and the leg portion 331 of the shell portion 330, the foot portion, relative to the leg portion 331, assumes the pes equinus position (FIG. 32).

The foot portion 332 and the leg portion 331 of the anterior shell portion 330, within the connecting area 339 of these two portions, possesses a window-like perforation 392 that extends approximately as far as into the lateral region of the foot portion 332 and the leg portion 331 so that the angle adapter 395 mounted on the shell portion 330 engages over this window-like perforation 392 in the form of a covering lug. The dimensions of the angle adapter is dimensioned in such a way that it is insertable into the window-like perforation 392 or can be placed with its circumferential rim upon the rim that delimits the window-like perforation 392 and is retained by means of clamping fit or force fit.

Figure 33:
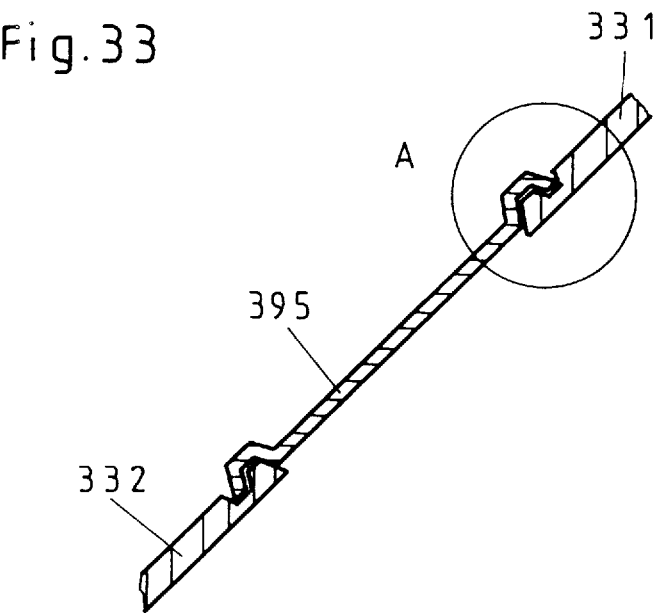
FIG. 33 shows a section in the direction of Line XXXIII—XXXIII in FIG. 31.

For mounting the angle adapter 395 on the wall areas of the foot portion 332 and of the leg portion 331 of the shell portion 330, the oppositely located edges 392a, 392b of the window-like perforation 392 that proceed transversally to the longitudinal direction of the leg portions possess on the outside bead-like or otherwise contoured strip-like reinforcements 393. At the same time, the angle adapter 395, on its upper rim 395a and lower rim 395b, is provided with the reinforcements 393 on the edges 392a, 392b with pertinently constructed counter contours in the form of marginal profiles 96. Thus, the angle adapter 395 is retained by means of clamping fit on the reinforcements 393 on the foot portion 332 or the leg portion 331 or on the same of the anterior shell portion 330 (FIG. 33).

Figure 34:
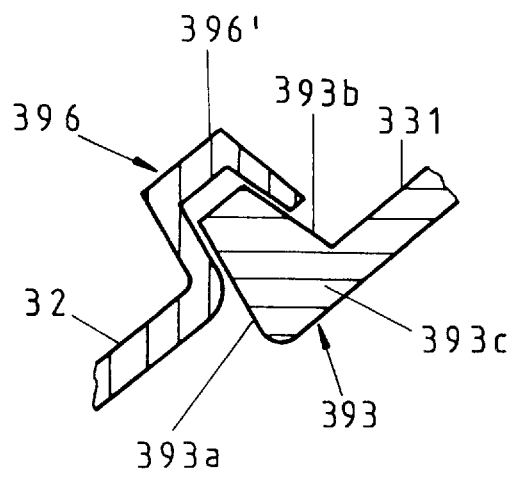
FIG. 34 shows an enlarged reproduction of the connecting section A between the angle adaptor and the wall area of the leg portion of the anterior shell portion.

The attachment and the mounting of the angle adapter 395 on the leg portion 331 and the foot portion 332 of the anterior shell portion 330 is effected with the aid of two locking hooks 398 disposed on the one end 395c of the angle adapter (FIG. 31). to be more precise, the locking hooks are disposed stationarily on the side of the inner wall, which engage into perforations 398' in the wall areas of the leg portion 332 of the shell portion 330. With this its end 395c, the angle adapter 395 is hooked into the provided perforations 398' in the wall areas of the leg portion 331 and of the foot portion 332 of the shell portion 330. On its other end 395d, the angle adapter 395 carries two rotatable locking hooks 399 which are constructed in the form of eccentrics, which likewise engage into pertinent perforations 399' in the wall areas of the leg portion 331 and of the foot portion 332, in which case the locking is performed by rotating the locking hooks 399 introduced into these perforations 399'. By means of these rotatable and eccentrically constructed locking hooks 399, the angle adapter 395 is stretched across the counter portions, in this case foot portions 332 and leg portion 331 so that a force fit free of play, especially on the oblique areas of the bead-like marginal reinforcements 393, is achieved thereby (FIG. 34). The number of the stationary locking hooks 398 and rotatable locking hooks 399 may be arbitrarily selected. It is essential, though, that in each case one stationary locking hook 398 and one rotatable locking hook 399 correspond to each other and engage into the perforations 399' in the foot portion 332.

It is possible, however, to employ otherwise constructed fastening means in lieu of locking hooks 398, 399.

By preference, the plate-shaped angle adapter 395 is comprised of a springably elastic material, expediently of a plastic.

The shell portions 320, 330 are also comprised of plastic.

According to an embodiment, the shell portions 320 or 330, preferably comprised of plastic, possess wall areas of solid wall construction. According to another embodiment, the wall areas of each shell portion 320 or 330 are latticed while forming perforations between intersecting lattice bars that may also be constructed in the form of strips or bands. This construction offers the advantage that a sleeve-like padding disposed between the wall of the shell-like member and the extremity is disposed in a positionally secured and slip-proof mode. This is because the easily deformable padding walls are pressed into the perforations of the wall lattice of the shell-like member in such a way that padding sections issue in a bead-like fashion from the perforations or come to lie in the same and are thus retained in their positions by the lattice bars which delimit the perforations.

A further possibility of the angular adjustability of the foot portion 332 relative to the leg portion 331 of the anterior shell portion 330 consists in that the foot portion 332 of the anterior shell portion 330 which is adjustable relative to the leg portion 331 is connected by means of a section 391 proceeding transversally to the longitudinal direction of the foot portion (FIG. 29). Section 391 is constructed in the manner of an accordion bellows, with a plurality of folded and film-hinge-like interconnected material strips 391a, in which case the swivel hinges 335 interconnecting the foot portion 332 and the leg portion 331 formed laterally on the shell-like member 310 are provided with angle locking means. In this embodiment, the area corresponding to the window-like perforation 392, which is otherwise closed with the aid of the plate-shaped angle adapter 395 between the foot portion 332 and the leg portion 331, is filled above a section 391 that comprises of the same material from which the shell portion 330 is also fabricated. This section 391 is constructed in a bellow-like fashion along the lines of an accordion or concertina, the individual strips of material 391a being connected in a film-hinge-like mode so that, in dependence of the respective angular position of the foot portion 332 in relation to the leg portion 331, the elongatable section 391 adapts itself to the same. The angle locking means provided within the area of the swivel hinges 335 is constructed in a manner known per se. The hinges comprise of fixating means, such as setscrews or the like, so that the preset angular position can be retained and be varied only subsequent to the angle locking means having been disengaged.

Figure 35:
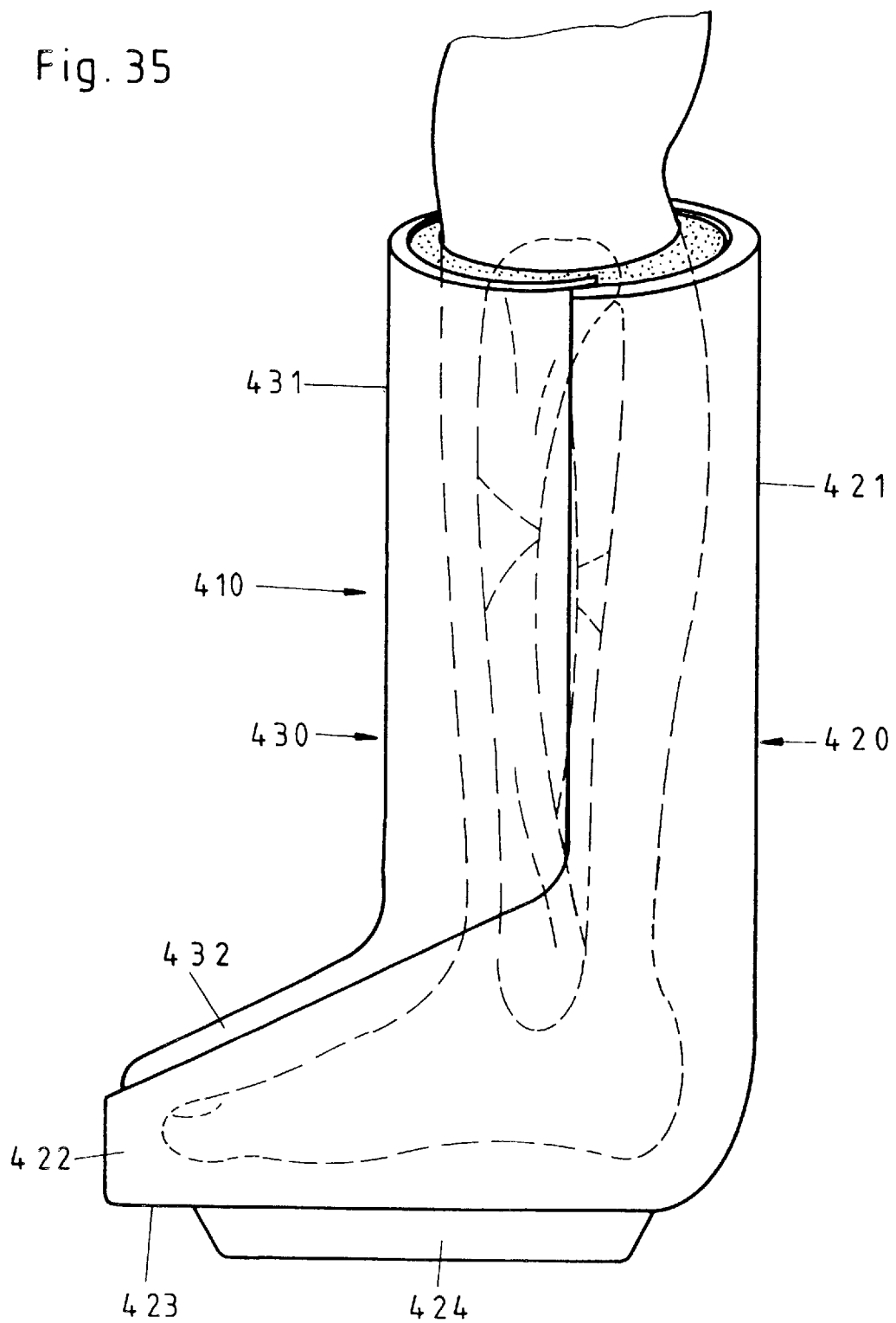
FIG. 35 shows a side view of the fixation device comprising a shell-like member with two L-shaped shell portions.
Figure 36:
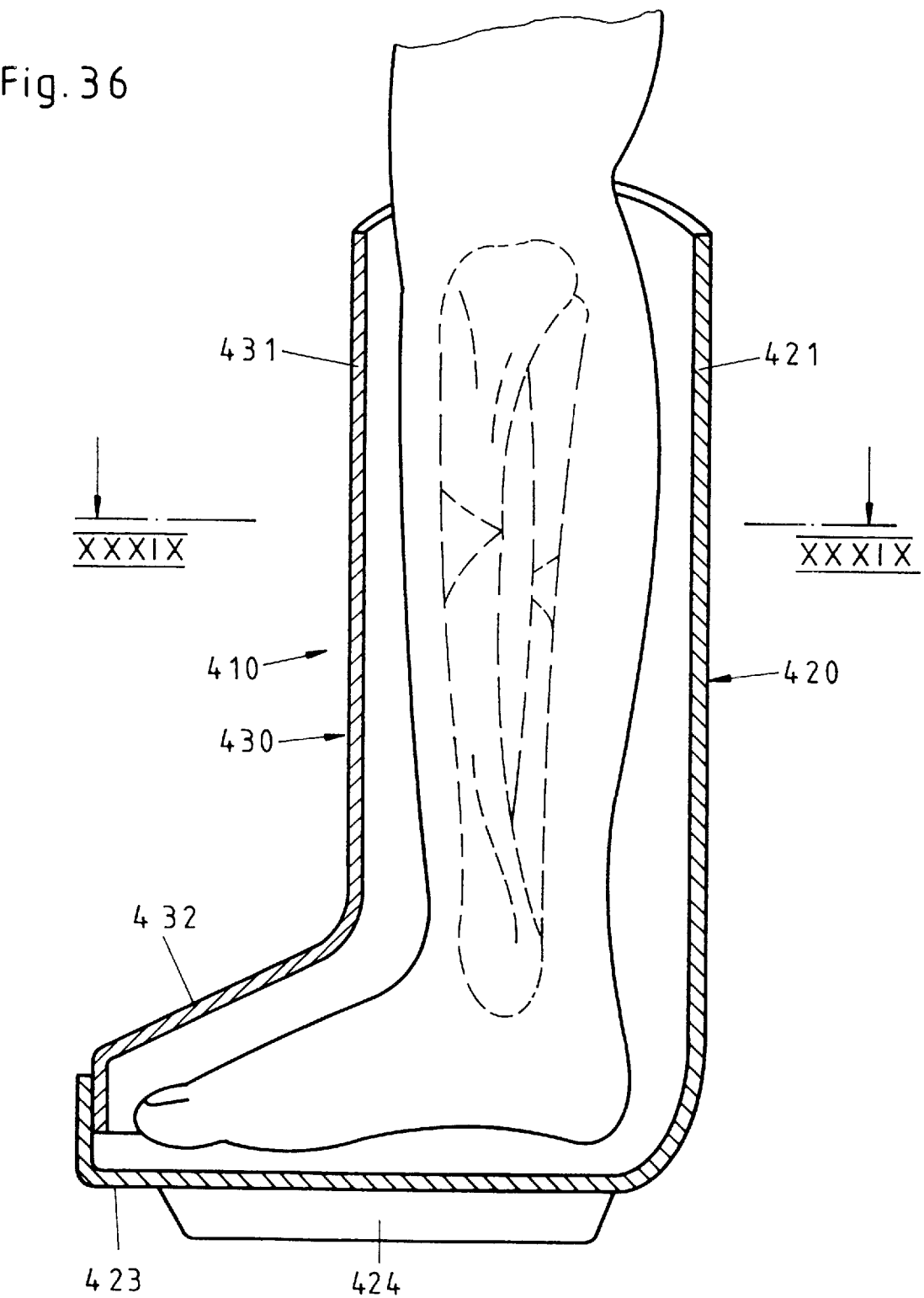
FIG. 36 shows the fixation device partly in a side view and partly in a vertical longitudinal section.

The device, according to FIGS. 35 and 36, is constructed in the form of a shell-like member for the foot/lower leg region of a patient.

The shell-like member 410 is comprised of two reciprocally tightened shell portions, viz. a posterior shell portion 420 and an anterior shell portion 430, in which case the two shell portions 420, 430 possess an approximately L-like configuration. Each shell portion 420 or 430 is comprised of a leg portion 421 or 431 and a foot portion 422 or 432, in which the foot portion 422 of the shell portion 420 can be connected to its leg portion 421 by means of lateral swivel hinges 35. Both the two shell portions 420, 430 as well as the hinges, comprise of plastic.

The foot portion 422 and the leg portion 421 of the posterior shell portion 420 are constructed in the manner of a shell open towards the top and in the forward direction to provide an accommodation trough for the foot and the lower leg. On the underside of the foot portion 422, an outsole 423 is provided, whose external configuration is adapted to the rolling movement of the foot when walking. For this purpose, the outsole 423 is constructed in the form of a walking rocker or is provided with a walking support 424.

The foot portion 432 and the leg portion 431 of the anterior shell portion 430 of the shell-like member 410 are constructed in a shell-like fashion in the direction towards the foot and the lower leg. This shell portion 430 is constructed such that the anterior shell portion 430 is insertable into the posterior shell portion 420 in such a way that the lateral wall sections of the shell portion 420 engage sectionwise over the lateral wall sections of the shell portion 430.

Figure 37:
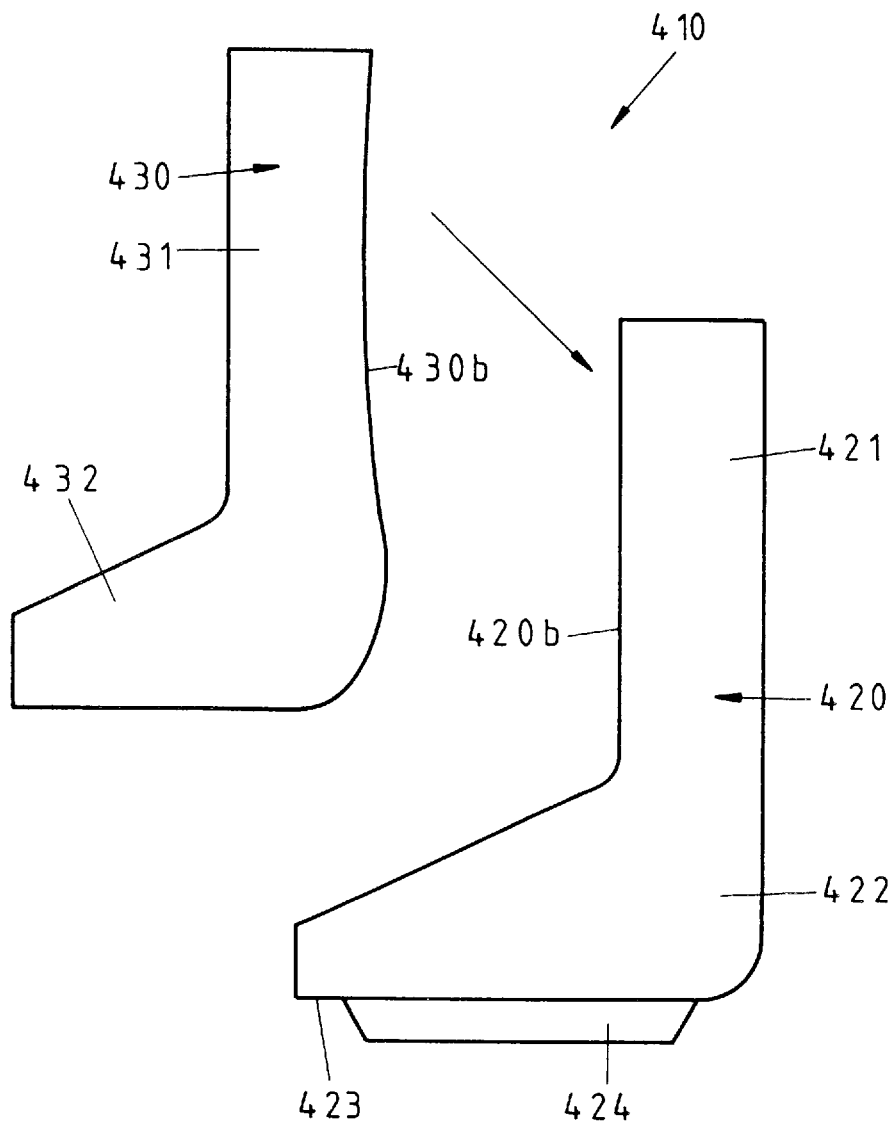
FIG. 37 shows in a side view the two L-shaped shell portions of the shell-like member prior to their being tightened.
Figure 38:
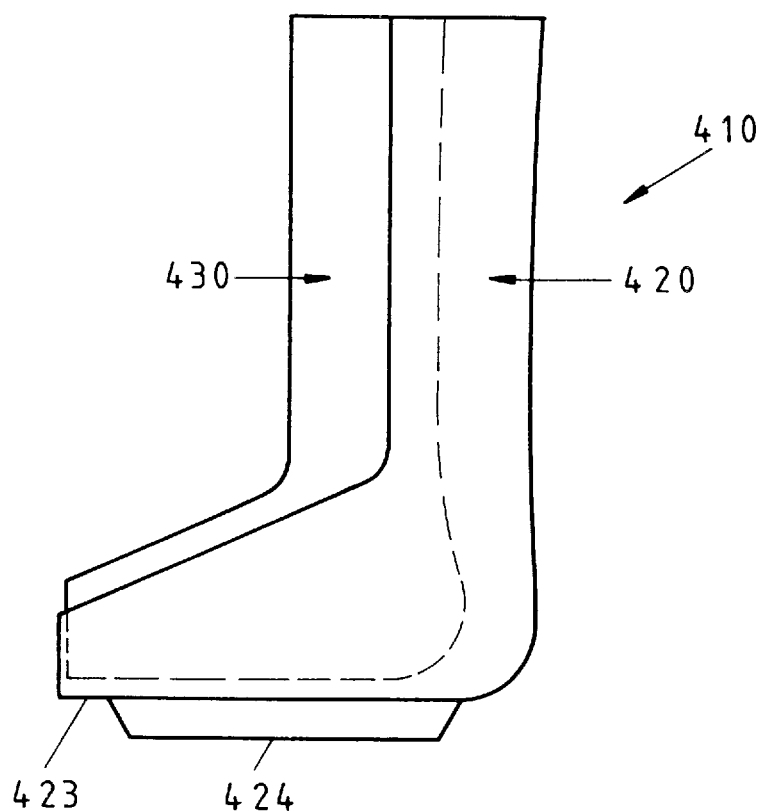
FIG. 38 shows a side view of the shell-like members.
Figure 39:
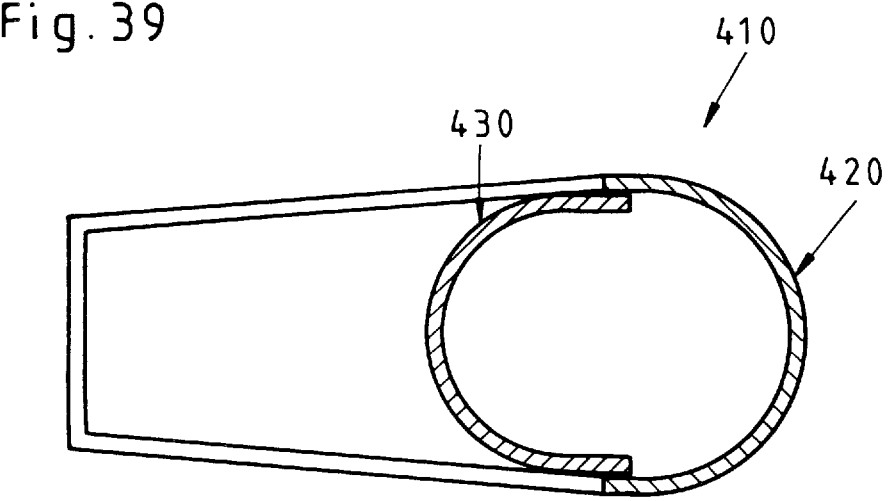
FIG. 39 shows a horizontal section in the direction of Line XXXIX—XXXIX in FIG. 36

Both the shell portion 420 and the shell portion 430 possess an approximately semi-circular cross-section so that, when the shell portions are placed inside each other, a section-wise engagement over the side wall sections of the two shell portions 420, 430 takes place (FIGS. 37, 38, 39). In order to laterally engage around the lower leg and also the foot, the shell portions 420, 430 possess a certain elasticity, in which connection the elasticity of the side walls of the two shell portions 420, 430 expediently increases from their central areas of the shell portions towards their free front edges 420b or 430b of each shell portion.

Between the two reciprocally tightenable shell portions 420, 430 and the extremity, a deformable, cushioning pad is provided (not shown in drawing) and constructed so as to be vacuum-tight and fitted with at least one valve that comprises of a bladder in which a great number of filling material particles are provided that are movable relative to each other. The cushion and sleeve-like padding which can be applied tightly and well fitting to the limb section to be treated, in the event of an evacuation which can be performed within a short period of time, becomes, while retaining the configuration it has acquired during the application procedure, hard and inherently stable. Then, in connection with the hard shell portions, a very sturdy sleeve well modeled onto the respective extremity is produced which is incapable of producing any pressure sores in the region of the skin since, during the consolidation of this object, no radial inwardly directed pressure is generated, nor can any edges or projections be formed on the inside either. In lieu of such a cushioning, sleeve-like padding, it is also possible to employ a different form of padding, a sock or the like for filling the interspace.

The closing or fastening means, provided on the longitudinal marginal areas of the foot portion and the leg portion, are especially comprised of Velcro strip fasteners. These closing means provide very simply and expeditiously for the slight bearing or contact pressure of the padding on the closed shell-like member, this pressure being necessary prior to the evacuation being effected. It is possible in this way to produce a sleeve possessing an absolutely correct fit and which can be fixated by means of the Velcro fastening strips. Once the evacuation has been performed, a sleeve is available that consolidates in itself, stabilized in its configuration and which retains the extremity in a positionally secured mode.

Figure 40:
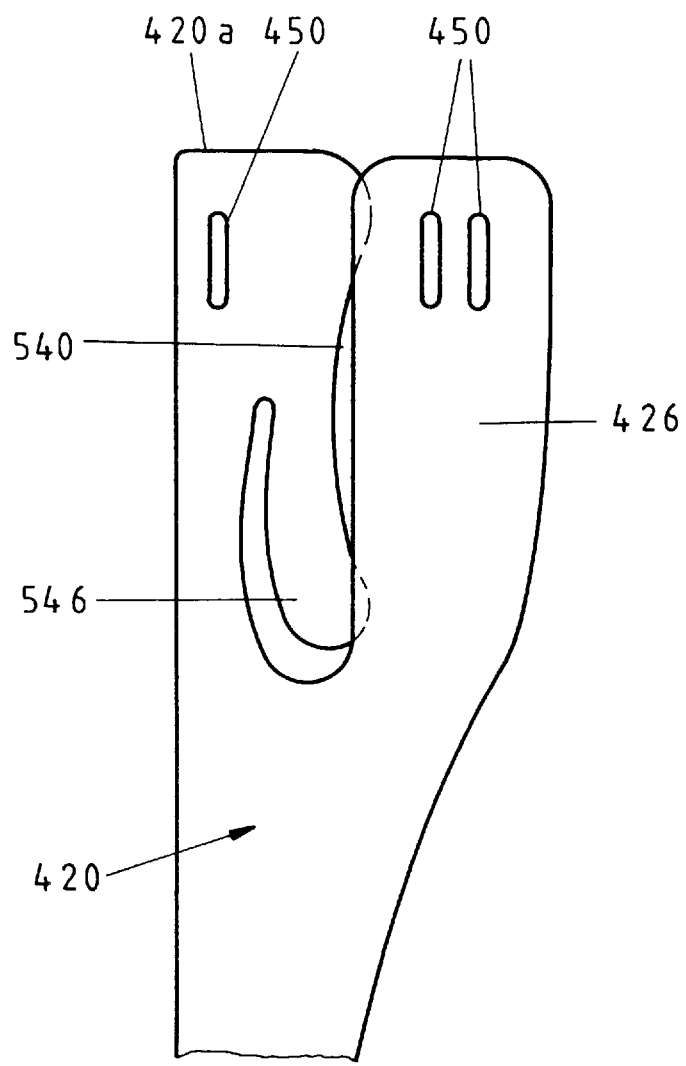
FIG. 40 shows a side view of the posterior shell portion.

In order to be able to adapt the shell-like member 410 to the respective existing calf sizes and configurations of the patient, the posterior shell portion 420 is provided with a plurality of slotted perforations 440, 540 setting out from its upper circumferential rim 20a, which extend in the longitudinal direction of the leg portion of the shell portion 420. In the embodiment that is illustrated in FIGS. 40 and 41, two slot-shaped perforations 440, 540 are provided in the rearward wall of the shell portion 420 which proceed parallel to each other and by means of which at least one section 445, which can be bent aside, is formed. The two slot-shaped perforations 440, 540 extend in the leg portion longitudinal direction of the shell portion 420 in such a way that, in the posterior shell portion 420, wall sections 425, 426, 445 are formed. These wall sections 425, 426, 445, with a means 460, can also be fixated in the requisite position (FIG. 41). The wall sections 425, 426 are stationary and have a stabilizing effect.

In the embodiment depicted in FIGS. 40 and 41, the two slot-shaped perforations 440, 540 are constructed so as to proceed in a U-like manner. The U-like perforation sections are indicated as 441, 541. Each slot-shaped perforation 440, 540 sets out from the upper rim 420a of the rearward side wall of the posterior shell portion 420 and proceeds, first of all, with section 443 in the longitudinal direction of the leg portion 421. This section 443 then passes into the U-shaped section 441, whose running-out leg section 442 is approximately parallel to the perforation section 443, as is illustrated in FIG. 41. The slot-shaped perforation 540 is constructed so as to correspond to the slot-shaped perforation 440 and is likewise formed by a section 543 proceeding in the longitudinal direction of the leg portion that is followed by the U-shaped section 541, whose leg section 542 proceeds parallel to the perforation section 443 so that the two perforations 440, 540 face each other. By virtue of this disposition and construction of slot-shaped perforations 440, 540 in the rearward wall of the shell portion 420, flap-like marginal sections 446, 546 are formed which have the effect of springably elastic tabs and which make it possible that the wall sections 425, 426, laterally delimiting the slot-shaped perforations 440, 540 of the posterior shell portion 420, allow themselves to be displaced against the springable sections 446, 546 in a way that an adaptation of the shell portion 420, and thus of the shell-like member 410, to the calf of the patient, is possible. This displaceability of the springably elastic wall sections of the posterior shell portion 420 is illustrated in FIG. 40.

The disposition of the two slot-shaped perforations 440, 540 takes place in the area of the posterior shell portion 420 of the shell-like member 410 that grips the calf of the lower leg of the patient.

Section 445, which can be bent aside, in the wall of the posterior shell portion 420 is connected with the wall of the same by means of a web 445', which is formed springably elastic onto the wall and retained, or is connected to the wall by means of a hinge connection so that section 445 possesses the function of a rocker and adapts itself to the calf and the movements of the calf muscle. Where a hinge connection is employed, a pressure relief of the calf occurs since the section 445 is virtually free-swinging, yet always in contact with the calf. Because of the hinge connection, which may also be constructed in the form of a film hinge, the section 445 is, together with its web 445', movable about the swivel axis 445a (FIG. 41).

In order to lock the posterior shell portion 420 of the shell-like member 410, subsequent to an effected adaptation to the calf of the patient in the adapted position, the springable and individually constructed sections 425, 426, 445 of the shell portion 420, which are adjacent to the upper circumferential rim 420a, possess a plurality of slot-shaped perforations 450 for receiving a strip-shaped fastening means 460. The fastening means 460 is constructed in the form of a belt strap or may comprise of portions of Velcro strip fastener in order to be able to fixate the posterior shell portion 420 in the adaptation position within the area of its leg portion 421. If the posterior shell portion 420 is employed without an anterior shell portion 430, the fastening elements act exclusively upon the stationary wall sections 425, 425. On these, the fastening elements may also be attached on one end. However, this kind of attachment is preferred in all cases since the free mobility of the sections 445 is not impaired by its web 445', in which case a longitudinal displaceability of the web towards the outside is also possible.

Consequently, the constructed fixation device is provided with an integrated calf adaptation without any impairment of the inherent stability of the shell-like member 410 being brought about by this. Despite the high degree of inherent rigidity, particularly of the posterior shell portion 420, an adaptation elasticity to the lower leg and to the calf of the patient exists. By means of an anterior shell portion 430 inserted into the posterior shell portion 420, a movement in the posterior shell portion 420 is prevented. The normal angular position between foot and lower leg of 90° can thus be, at all times, adhered to. When undergoing inpatient treatment after an operation, the lower leg of the patient is located in the posterior shell portion 420 and is fixated in the same so that it is possible to retain the correct anatomical position. Despite the fixation of the foot and of the lower leg in the normal angular position of 90°, a high degree of stabilization is achieved.

In order to achieve an adaptability of the posterior shell portion 420 to the calf, it is also possible for the rear wall and/or the side walls of the shell portion 420 to be constructed differently and to possess notches proceeding as in the aforedescribed slot-shaped perforations 440, 540. Since the shell portion 420 is comprised of plastic, the possibility exists of providing, in lieu of slot-shaped perforations 440, 540, sections proceeding in the longitudinal direction of the shell portion in the form of material attenuations that become deformed in a concertina-like fashion when the individual wall sections are displaced against each other.

I claim:

1. A device for the ensheathing fixation of extremities and extremity regions of a leg of a human body, said device comprising:

a first L-shaped posterior shell portion having a swivellable foot portion, said foot portion swivellable by a first hinge;

a second L-shaped anterior shell portions, said posterior and anterior shell portions being reciprocally tightenable and having a substantially semicircular cross-section which surround the extremity so that said posterior and said anterior shell portions are coupled one to another, said anterior shell portion provided with a swivellable foot portion attached to said anterior shell portion by a second hinge, said first and second hinges being angularly adjustable;

said first and second shell portions are provided with an irregular lattice structure extending over the surface of each shell portion, said irregular lattice structure comprised of a plurality of longitudinal ribs and a plurality of transverse ribs, at least one of said plurality of longitudinal ribs being a longitudinal structural ribs for each of said L-shaped shell portions, said longitudinal rib and said transverse ribs intersecting at an attachment point, said attachment point having a width greater than the width of said transverse ribs;

said longitudinal structural ribs provided respectively for said first and second shell portions which extend substantially over the length of the first and second shell portions, said longitudinal structural ribs having a diameter greater than said longitudinal and transverse ribs;

a removable sleeve cushioning pad positioned within said first and second L-shaped shell portions, said cushioning pad provided with filler material particles movable relative to each other; and means for adjusting the width of said first and second L-shaped shell portions and for adjusting the longitudinal structural ribs.

2. The device as set forth in claim 1, wherein the width of said plurality of longitudinal and transverse ribs are in the range of 1.5 cm to 3 cm.

3. The device as set forth in claim 1, wherein said plurality of longitudinal and transverse ribs are provided with varying widths.

4. The device as set forth in claim 1, wherein said foot portion of said second L-shaped posterior portion is adjustable relative to said leg portion of said anterior shell portion by a plurality of folded hinged interconnected strips.

5. The device as set forth in claim 1, further comprising angle adjustment means which comprises an angle adapter disposed between said foot portion and said leg portion of said anterior shell portion, said angle adapter being detachably retained on said leg portion of said anterior shell portion.

6. The device as set forth in claim 5, wherein said angle adjustment means adjusts the foot portion of said anterior shell portion, relative to the leg portion of the anterior shell portion, to an angular position of 90.

7. The device as set forth in claim 5, wherein said angle adjustment means adjusts the foot portion of the anterior shell portion, relative to the leg portion of the anterior shell portion, to an angular position of 120.

8. The device as set forth in claim 5, wherein the angle adjustment means is comprised of a springably elastic material.

9. The device as set forth in claim 5, wherein the two shell portions and the angle adjustment means are fabricated from plastic.

10. The device as set forth in claim 4 wherein the posterior shell portion comprises:

a foot portion that is angularly adjustable to the leg portion; and a window-like perforation, located in the wall area opposite the foot portion, with a replaceable angle adapter, said angle adapter having an engagement recess for engaging a pin, said pin being in the rear of the foot portion to allow setting of a predetermined angular position.

11. The device as set forth in claim 10, wherein said angle adjustment means may be provided with varying positional arrangements of the engagement apertures which are insertable into the window-like perforation.

12. The device as set forth in claim 10, wherein said window-like perforation is approximately rectangular, and said angle adjustment means is constructed to correspond with the configuration and dimension of the window-like perforation.

13. The device as set forth in claim 10, wherein an engagement aperture is constructed in the lower area of said angle adjustment means.

14. The device as set forth in claim 10, wherein an engagement aperture is constructed in the upper area of said angle adjustment means.

15. The device as set forth in claim 10, wherein said angle adjustment means is provided with a slot-shaped engagement aperture.

16. The device as set forth in claim 10, wherein said angle adjustment means comprises a plurality of circumferential grooves on its circumferential rim that extend across oppositely located areas for engagement of said rim to delimit the window-like perforation.

17. The device as set forth in claim 10, wherein said angle adjustment means comprises a springably elastic material with aid of a clamping fit that is retained on the window-like perforation's circumferential rim.

18. The device as set forth in claim 10, wherein said angle adjustment means possesses an uniformly upwardly expanding reinforcement of a springably elastic material on its two longitudinal marginal sections.

19. The device as set forth in claim 10, wherein said angle adjustment means is provided with first and second perforations in its upper area and spaced apart from each other.

20. The device as set forth in claim 10, wherein said pin has a setscrew shape.

21. The device as set forth in claim 1, wherein the foot portion and the leg portion of the anterior shell portion are provided with a window-like perforation within the area between said foot and leg portions.

22. The device as set forth in claim 1, wherein said window-like perforation is provided with beaded edges so as to connect said window like perforation with said foot and leg portions of said anterior shell portion, and where the angle adjustment means is retained on the anterior shell portion.

23. The device as set forth in claim 22, wherein the beaded edges on the foot portion and the leg portion of the anterior shell portion have a substantially square, conically upwardly proceeding lateral surface area.

24. The device as set forth in claim 1, wherein said angle adjustment means is provided with at least two stationary locking hooks which engage into the wall areas of the leg and foot portions of said anterior shell portion, and wherein the angle adjustment means is provided with at least two rotatable locking hooks which engage into corresponding perforations in the wall areas of the leg portion and foot portion of the anterior shell portion.

25. The device as set forth in claim 1, wherein said removable cushioning pad is disposed on the insides of the shell portions.

26. The device as set forth in claim 1, wherein said leg portion of said anterior shell portion are provided with two adjustable guide ways.

27. The device as set forth in claim 26, wherein one guide way projects over the other in the direction of the longitudinal axis of the upper shell portion by a length that is at least equal to the length of the connecting element, and wherein one guide way is substantially constructed up to the edge of the upper shell portion.

28. The device as set forth in claim 26 further comprising a connecting element which is restrictably displaceable in the direction of the rim of the upper leg portion.

29. The device as set forth in claim 1 wherein the upper leg portion is provided with two guide ways proceeding substantially parallel, said ribs engaging into pertinently configured grooves of sliding member that is longitudinally displaceable, and said ribs being non-removable from the side.

30. The device as set forth in claim 29, wherein the guide ways are dovetailed.

31. The device as set forth in claim 29, further comprising a sliding member, wherein the sliding member engages over two longitudinal ribs of the upper leg portion and is guidable over the upper leg portion.

32. The device as set forth in claim 1 wherein the spaced-apart longitudinal ribs are provided with bead-like raised points that constitute guide rails.

33. The device as set forth in claim 1 wherein said foot portion of said anterior shell portion is angularly adjustable relative to leg portion of the anterior shell portion, said leg portion having an angle adjustment means, said angle adjustment means allowing the foot portion to lock at a predetermined angular position relative to the leg portion, and wherein said posterior shell portion possesses a foot portion, the foot portion being angularly adjustable in relation to leg portion of the posterior shell portion.

34. The device as set forth in claim 33, wherein said foot portion of the anterior shell portion is connected with a plurality of folded, film hinge-like interconnected strips of material by means of an accordion bellows-like constructed section, in which swivel hinges interconnecting the foot portion and the leg portion are provided with angle locking means.

35. The device as set forth in claim 33, wherein said angle adjusting means is comprised of an angle adapter, said angle adapter being disposed between the foot portion and the leg portion of the anterior shell portion and configured to correspond with the anterior shell portion, said angle adapter being detachably retained by means of a click-stop and locking means on the leg portion and the foot portion of the anterior shell portion.

36. The device as set forth in claim 33, wherein said angle adapter possesses a width that allows the foot portion in relation to the leg portion of the anterior shell portion to assume an angular position of 90.

37. The device as set forth in claim 33, wherein said angle adapter possesses a width that allows the foot portion in relation to the leg portion of the anterior shell portion to assume an angular position of 120.

38. The device as set forth in claim 33, wherein the anterior shell portion possesses a window-like perforation in the area connecting foot portion and leg portion, said perforation extending into lateral areas of the foot portion and the leg portion, and disposing the angle adapter.

39. The device as set forth in claim 38, wherein the ribs reinforcements are provided with a rectangular cross-section.

40. The device as set forth in claim 33, wherein said angle adjustment means is provided with ribbed reinforcements on its upper and lower rim.

41. The device as set forth in claim 33, wherein said angle adjustment means is provided with at least two stationary locking hooks on the side of the inner wall that engage into perforations in the wall areas of the leg portion and foot portion of the anterior shell portions.

42. The device as set forth in claim 33, wherein said angle adapter comprises of a springably elastic material.

43. The device as set forth in claim 1 wherein the posterior shell portion is provided with slot-shaped perforations that extend over an area in the longitudinal direction of the shell portion, said posterior shell portion having springably elastic and reciprocally displaceable wall sections.

44. The device as set forth in claim 43, wherein two spaced-apart slot-shaped perforations are constructed, said perforations proceeding in the longitudinal direction of the shell portion and extending from the upper shell portion rim, said perforations further running into approximately U-shaped section having slot-shaped leg sections proceeding parallel to each other.

45. The device as set forth in claim 43, wherein a web constructed between slot-shaped leg sections is springably elastically retained on the wall of the posterior shell portion.

46. The device as set forth in claim 42, wherein a web constructed between slot-shaped leg sections is connected to the wall of the posterior shell portion by means of a hinge connection.

47. The device as set forth in claim 43, wherein the posterior shell portion possesses a plurality of slot-shaped perforations.

48. The device as set forth in claim 43, wherein slot-shaped perforations are provided in the posterior shell, adjacent to the upper shell portion rim, for receiving fastening elements.

49. The device as set forth in claim 48, wherein the fastening elements are secured to the wall sections of the posterior shell portion.

* * * * *